US009897596B2

United States Patent
Kellogg et al.

(10) Patent No.: US 9,897,596 B2
(45) Date of Patent: Feb. 20, 2018

(54) MICROFLUIDIC DISC FOR USE IN WITH BEAD-BASED IMMUNOASSAYS

(75) Inventors: Greg Kellogg, Cork (IE); Jerry O'Brien, Cork (IE); Eoin O'Nuallain, Cork (IE); Damian Curtin, Cork (IE)

(73) Assignee: Radisens Diagnostics Limited, Cork (IE)

(*) Notice: Subject to any disclaimer, the term of this patent is extended or adjusted under 35 U.S.C. 154(b) by 684 days.

(21) Appl. No.: 14/123,625

(22) PCT Filed: Jun. 5, 2012

(86) PCT No.: PCT/IE2012/000026
§ 371 (c)(1),
(2), (4) Date: May 9, 2014

(87) PCT Pub. No.: WO2012/164552
PCT Pub. Date: Dec. 6, 2012

(65) Prior Publication Data
US 2014/0242721 A1    Aug. 28, 2014

Related U.S. Application Data

(60) Provisional application No. 61/493,234, filed on Jun. 3, 2011.

(30) Foreign Application Priority Data

Jun. 3, 2011    (EP) .................................... 11168702

(51) Int. Cl.
*B01L 3/00*    (2006.01)
*G01N 33/53*    (2006.01)
*G01N 33/543*    (2006.01)

(52) U.S. Cl.
CPC .... *G01N 33/5304* (2013.01); *B01L 3/502753* (2013.01); *G01N 33/543* (2013.01);
(Continued)

(58) Field of Classification Search
None
See application file for complete search history.

(56) References Cited

U.S. PATENT DOCUMENTS

| 2004/0089616 | A1 | 5/2004 | Kellogg et al. |
| 2004/0096867 | A1 | 5/2004 | Andersson et al. |
| 2008/0073546 | A1* | 3/2008 | Andersson .......... B01F 13/0059 250/396 ML |

FOREIGN PATENT DOCUMENTS

| WO | 9853311 A2 | 11/1998 |
| WO | 2006110098 A1 | 10/2006 |

OTHER PUBLICATIONS

PCT International Preliminary Report on Patentability for PCT International Application No. PCT/IE2012/000026, dated Dec. 19, 2013, 6 pages.

* cited by examiner

*Primary Examiner* — Rebecca L Martinez
(74) *Attorney, Agent, or Firm* — K&L Gates LLP

(57) ABSTRACT

The invention relates to a microfluidic system for processing biological samples comprising a rotary motor; a means for controlling said motor; a platform coupled to the rotary motor and adapted to provide at least one particle-washing structure and one particle receiving structure for receiving washed particles; and a detection zone for detection of particles of the sample in the particle receiving structure while the platform rotates. The invention provides a sample processing system that is both automated and prone to fewer errors than manual processing. This is accomplished using a centrifugal microfluidic platform that can process raw biological samples (e.g., blood, sputum, urine,) in order to perform high-quality bead-based immunofluorescent assays.

(Continued)

The invention uses a simple rotary motor and custom-designed plastic disc to perform the sample preparation steps outlined above.

15 Claims, 25 Drawing Sheets

(52) U.S. Cl.
CPC *G01N 33/54366* (2013.01); *B01L 2200/0636* (2013.01); *B01L 2200/0652* (2013.01); *B01L 2200/0684* (2013.01); *B01L 2300/0681* (2013.01); *B01L 2300/0803* (2013.01); *B01L 2400/043* (2013.01); *B01L 2400/0409* (2013.01); *B01L 2400/0677* (2013.01); *B01L 2400/0688* (2013.01); *B01L 2400/086* (2013.01); *B01L 2400/088* (2013.01)

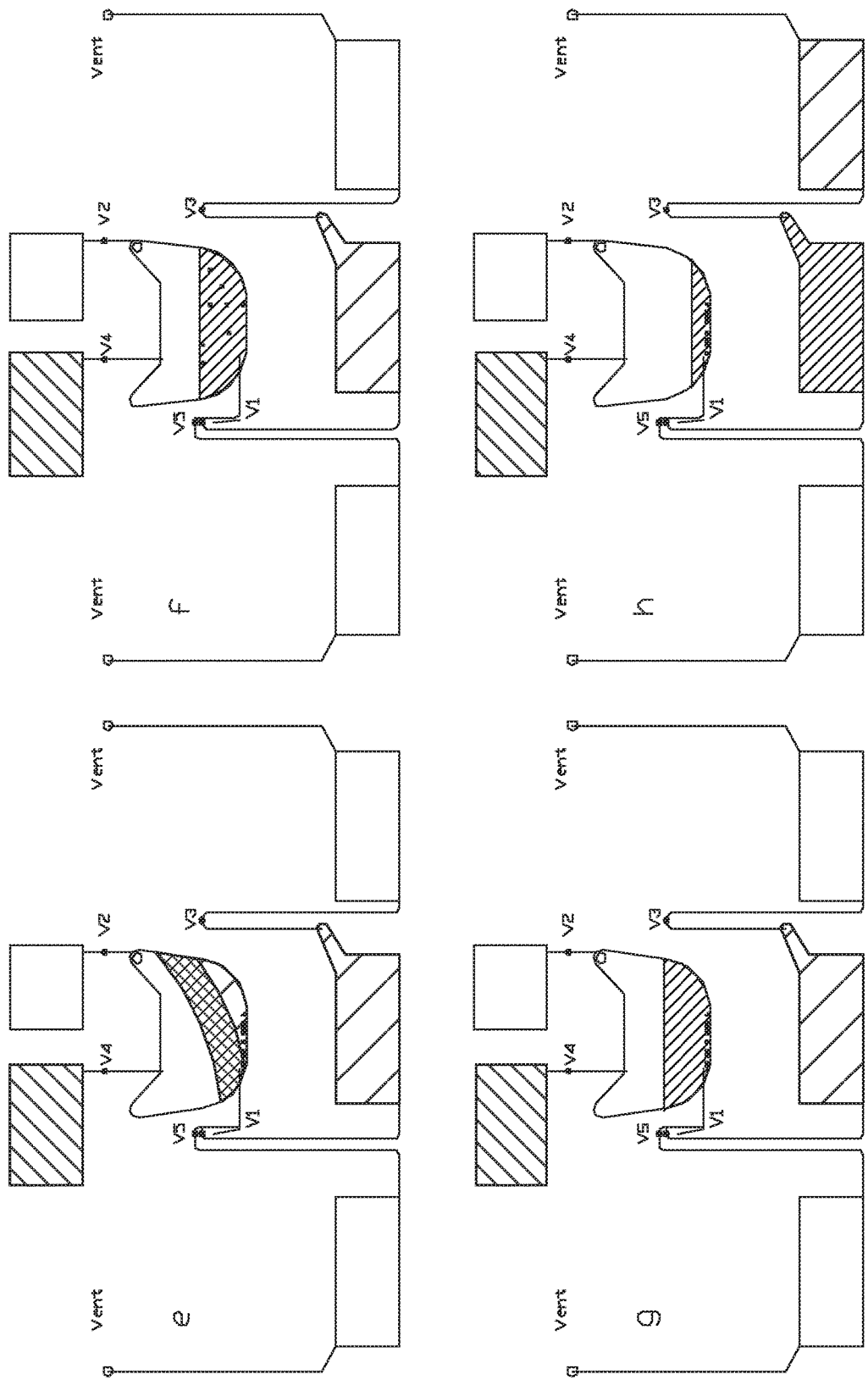

Focus at 10:1 flow ratio 3-sample combined immunoassay and clinical chemistry disc

MICROFLUIDIC DISC FOR USE IN WITH BEAD-BASED IMMUNOASSAYS

CROSS REFERENCE RELATED APPLICATIONS

This application is a national phase under 35 U.S.C. § 371 of International Application No. PCT/IE2012/000026 filed on Jun. 5, 2012, which claims the benefit of and priority to European Patent Application 11168702.6 and U.S. Provisional application 61/493,234 both filed on Jun. 3, 2011, the entire disclosures of each of which are incorporated herein by reference.

FIELD OF THE INVENTION

The invention relates to a microfluidic disc, apparatus, system and method, for use in immunoassay diagnostics or in a portable diagnostic analyser.

BACKGROUND TO THE INVENTION

Flow cytometry is a powerful method of analysis to determine the cellular/biological content of various types of samples, and in particular samples that contain living cells. In clinical applications, flow cytometers are useful for myriad of applications including lymphocyte counting and classification, for immunological characterization of leukaemias and lymphomas, leukocyte counting and classification, and bead-based immunoassay diagnostics.

In most flow cytometry techniques, cells in a fluid solution are caused to flow individually through a light beam, usually produced by a laser light source or a monochromatically filtered LED source. As light strikes each cell, the light is scattered and the resulting scattered light is analyzed to determine the type of cell. The cell may also optionally be labelled with a marker linked to a fluorescent molecule, which fluoresces when light strikes it and thereby reveals the presence of the marker on the cell. In this fashion, information about the surface components of the cell can be obtained.

Fluorescent beads provide a convenient and powerful method for performing multiplexed immunoassays. For example, multiplexing may be achieved by using beads of different colours (either scattered or fluorescence emission) coupled with analytes that are uniformly dyed with another distinct colour. In this way, the assay identity may be read from the bead colour/fluorescence while the analytic result can be read from the amount of fluorescent dye bound to the bead. Beads also provide a format in which solid phases of immunoassays may be manufactured in bulk, increasing the robustness of assays. Typically, flow cytometers are used to perform multiplexed, bead-based immunoassays, by virtue of their ability to detect and quantify fluorescence from particles.

One significant problem with currently implemented immunofluorescent bead assays is that they require extensive manual or robotic sample processing. For a sandwich-type immunoassay, this sample processing may consist of some or all of the following steps:

separation of plasma from whole blood
metering of plasma to provide known volume of starting sample
dilution of plasma
mixing of dilute sample with immunofluorescent beads to promote binding of analyte
incubation for sufficient time and at a temperature appropriate for binding
washing of beads
mixing of washed beads with labelled secondary antibody to promote binding
incubation for sufficient time and at a temperature appropriate for binding
washing of unbound secondary antibody
injection of beads into flow cytometric flow channel.

Manual processing is cost-prohibitive in many applications and is also prone to errors. Automation is also cost-prohibitive in many applications, and is inappropriate as currently practiced—using, for example, liquid handling robots—for applications such as point-of-care or doctor's office analysis. As a result, there is an unmet need to provide sample processing for multiplexed, bead-based immunoassays that is less expensive and less prone to error than current automation or manual processing.

A drawback of Point-of-Care diagnostic assay systems is that they are typically incapable of multiplexing a variety of assay types. While these systems are quite good at performing a variety of similar assay types—such as lateral flow assays, or electrochemical assays, etc.—the assay conditions required of different kinds of assays—such as immunoassay vs. colorimetric blood chemistry—make them inappropriate for multiplexing these different assay types. Again, centralized laboratories may achieve such integration by splitting samples and performing the assays in different devices. The centrifugal microfluidic platform with optical detection allows for a variety of assay technologies to be implemented in parallel using a single instrument and disposable.

A further significant problem of currently implemented immunofluorescent bead assays is that they are run on instruments developed for hematologic flow cytometry. While these instruments are capable of performing these assays, they are both expensive and complex, requiring significant maintenance and calibration. As a result, there exists a need for low-cost and low-maintenance instrumentation for performing such assays.

Furthermore, immunofluorescent bead assays are typically implemented using sheath flow, in which beads are diluted and aligned by the focusing flow of a buffer around the bead liquid stream. This has the dual effect of separating particles from one another such that they are not simultaneously within the detection volume of the instrument and positioning them in roughly the same place in the optical system. While this is very useful for hematologic assays, it does not confer any advantage for the detection of large numbers of essentially identical objects, such as fluorescent beads, and greatly complicates the functioning of the system. Similar statements hold if the bead sample consists of two or more well-defined populations differentiated for example by emission spectrum of their fluorescent labels.

In cases where sheath flow may be desired—extremely highly multiplexed immunoassays, or hematologic assays run on the same system as the immunoassay system—the centrifugal format provides a significant advantage over conventional pump-based systems. In the latter, typically multiple pumps are used for sample and sheath fluid flow, and great care must be taken to minimize the pulsatility of the pumps, maintaining a defined, smooth flow and ratio between sample and sheath flow. Because pumping due to centrifugal force is pulseless, such variations are inherently not present in the system.

A number of methods and devices exist for performing Bead-Based Immunoassays.

US patent publication number US2004/096867, Anderson et al, describes a system with trapped beads that are "washed through", one weakness with this US patent publication is that it does not provide a means for moving beads from one point to another, making single bead detection impossible. A further weakness is that systems with trapped beads forming the solid phase require manufacturing techniques that are demanding. For example, in order to provide highly reproducible binding of analyte molecules and fluorescent labels, the packed 'bed" of beads must be reproducibly structured; poor packing of the beads can lead to channels within the bead bed that pass analyte rapidly, without sufficient time for binding, resulting in low binding efficiency.

PCT Patent Publication number WO2006/110098, Gyros Patent AB, discloses a centrifugal based microfluidic device that comprises a microchannel structure in which there is a detection microcavity which in the upstream direction is attached to an inlet microconduit for transport of liquid (transport microconduit) to the detection microcavity and which is used for detecting the result of a reaction taking place in the detection microcavity or in a reaction microcavity positioned upstream of the detection microcavity. This application is primarily directed toward providing means for generating fluid "plug" flow and for joining fluids without bubbles or blockages and requires hydrophobic surface treatment for valves. The feature sizes for such structures have been realized using extensions for compact disc compression/injection moulding technology, which is incapable of producing structures which can hold larger volumes that are clinically relevant (e.g., 10 s to 100 s of uL). Discs manufactured by Gyros typically have features <=0.5 mm deep and do not operate for small or tiny volumes.

In WO9853311A2, Gamera Bioscience Corp, devices are disclosed for the performance of competitive immunoassays on a microfluidic disc. These are performed using a stationary solid phase—e.g., antibodies dried within a chamber on the disc. Furthermore, detection is via color-formation by a substrate specific for binding.

Binding of antibody directly to disc materials presents manufacturing difficulties which can be avoided by binding the antibodies instead to a "mobile" solid phase such as beads. There is no need for coating disc structures and maintaining them in the wet state for significant reaction times. Beads may also be processed in bulk quantities sufficient for hundreds of thousands of disposables under optimal conditions, including vigorous agitation to enhance reaction kinetics during their conjugation with capture antibodies.

Detection via colorimetric substrate is attractive in that it allows amplification of signal through the enzymatic reaction causing the build-up of color, but it is far more sensitive to temperature variations than is a simple fluorescent-binding assay. This temperature-sensitivity also makes storage of enzyme-based reagents for long periods (long shelf life) difficult.

In US20040089616, Kellogg et al. discloses a microfluidic disc for evaluation of glycated haemoglobin, total haemoglobin, and glucose in whole blood. One portion of the microfluidic disc uses an affinity matrix comprised of agarose beads retained between frits within the flow path of lysed, dilute blood: The glycated fraction is bound to the beads as it flows through, and the non-glycated fraction is measured photometrically in a cuvette. Combined with the measurement of total haemoglobin in another cuvette, this provides the glycated haemoglobin fraction. There are several problems to this formatting of an affinity method. First, retention of the beads requires either a) inserted elements, such as frits or b) channel constrictions in 1 dimension ("weirs", which are too shallow for the passage of a bead) or 2 dimensions to retain the solid phase beads. In each case, manufacturing requirements are significant, requiring specialized methods for the production of features as low as a few to a few tens of microns. It is preferable to manufacture devices using more conventional methods such as the machining of injection moulding tools followed by injection moulding.

It is therefore an object of the invention to provide an immunoassay diagnostics device, system and/or method to overcome at least one of the above mentioned problems.

SUMMARY OF THE INVENTION

According to the invention there is provided, as set out in the appended claims, a microfluidic system for processing biological samples comprising:
  a rotary motor;
  a means for controlling said motor;
  a platform coupled to the rotary motor and adapted to provide at least one particle-washing structure and particle receiving structure adapted for receiving particles washed in the particle washing structure; and
  a detection zone for detection of washed particles in the particle receiving structure while the platform rotates.

The present invention provides a sheathless flow method appropriate for immunoassays which removes the complexity of sheath flow.

The invention provides a sample processing system that is both automated and prone to fewer errors than manual processing. It is also cost-effective relative to robotic systems. This is accomplished using a centrifugal microfluidic platform that can process raw biological samples (e.g., blood, sputum, urine,) in order to perform high-quality bead-based immunofluorescent assays. The invention uses a simple rotary motor and custom-designed plastic disc to perform the process using a novel particle washing structure and particle receiving structure combination on a single platform.

The invention also provides means for detection of beads in a flow-channel on the microfluidic disc while undergoing rotation. In one embodiment, the beads (or particles) are injected into the flow channel without the use of additional flow focusing due to sheaths, magnetism, inertial forces or other focusing means. This greatly simplifies the device architecture required to perform assays.

In one embodiment the particles are immuno-modified beads and/or fluorescently labelled immuno-modified beads representative of characteristics of said biological sample.

In one embodiment the detection zone is adapted to cooperate with an optical system while the platform rotates.

In one embodiment the particle receiving structure comprises a pelleting chamber. In one embodiment the pelleting chamber is tapered to a point at one end such that the detection zone at its outermost point is defined.

In one embodiment the tapered end further comprises an elongated thin channel portion closed at one end to allow beads to sediment in the channel under centrifugal force.

In one embodiment the detection zone is shaped such that the particles are compacted into a small area upon pelleting by centrifugation.

In one embodiment the particles are washed in a reservoir that is adapted for the sedimentation of beads against the wall distal from the centre of rotation under the influence of centrifugal force.

In one embodiment the particle receiving structure comprises a flow channel.

In other embodiments, sheath flow is employed. In these cases, simple 1-dimensional sheaths can be created using centrifugal force and easily-created microfluidic disc topologies, greatly decreasing the probability of multiple counting.

In other embodiments, multiplexed assay types are performed. For example, immunoassays using flow cytometric detection of beads can be combined with colorimetric detection of enzymatic assays performed using reflectance or bulk optical density (OD) measurement.

In another embodiment there is provided a microfluidic system for processing biological samples comprising:
  a rotary motor;
  a means for controlling said motor;
  a platform coupled to the rotary motor and adapted for receiving particles; and
  means for detection of particles of the sample in the flow-channel while the platform rotates.

In one embodiment the particles are immuno-modified beads.

In one embodiment the particles are washed in a reservoir that is adapted for the sedimentation of beads against the wall distal from the centre of rotation under the influence of centrifugal force.

In one embodiment the washing reservoir has a bifurcated outlet channel which leads both to a waste reservoir and a flow channel.

In one embodiment the geometric constrictions of capillary dimensions and expansions within the bifurcations of the outlet channel act to resist flow at a first rotational velocity of the platform when the washing reservoir contains fluid but allow fluid to flow at a second higher rotational velocity.

In one embodiment the quotient of radial position of the constriction and diameter of the constriction for the bifurcation leading to the flow channel is smaller than the quotient of the radial position of the constriction and diameter of the constriction for the bifurcation leading to the waste reservoir.

In one embodiment the outlet channel emerges from the wash reservoir at a radius that is less than the maximum radial position of the radially distal wall of the wash reservoir, such that a defined volume will be retained within the washing reservoir when emptying into the waste reservoir in response to centrifugal force.

In one embodiment the retained fluid contains particles.

In one embodiment the waste reservoir has a defined volume equal to the desired sample volume minus the retained volume.

In one embodiment a channel is provided to carry air displaced from the waste reservoir.

In one embodiment the channel is directed radially inward from the waste reservoir, ending at a port or other channel at a radial position interior to the innermost liquid level to be achieved within the washing reservoir while the platform is under rotation and the washing chamber is filled with the maximum volume of operating fluid.

In one embodiment the interior volume of the reservoir is greater than that of the maximum designed volume of operating fluid, to enable the use of air within the reservoir in mixing the fluid while under rotational accelerations and decelerations.

In one embodiment the flow channel leads directly from the wash reservoir to a waste reservoir, without further channel bifurcations/junctions.

In one embodiment the flow channel leads without bifurcation or junctions to a second waste reservoir.

In one embodiment a port or channel terminated by a port or other channel is used to evacuate air displaced from the waste reservoir by fluid flowing through the flow channel.

In one embodiment the flow channel is configured in a substantially azimuthal orientation on the platform.

In one embodiment the flow channel length and diameter are chosen to ensure that the velocity of the fluid streamline at the centre of the channel multiplied by the rotational period of the platform and divided by the length of the channel to ensure that each particle is detected at least once per rotation.

In one embodiment there is provided a method for washing particles comprising one or more of the following steps of:
  configuring a platform as described in claim 1 adapted to provide at least one particle-washing reservoir and one flow channel for receiving washed particles;
  providing a mixture of particles and solution within the washing reservoir in a defined volume;
  providing a second solution of volume greater than the first solution within a buffer reservoir;
  rotating the platform at a first rotational velocity for time sufficient to sediment the particles against the distal wall of the washing reservoir
  increasing the rotational velocity such that the pressure exceeds the capillary pressure required to deliver fluid through the waste channel to the first waste reservoir, thereby draining all fluid except for a defined amount containing the sedimented particles, into the waste reservoir;
  momentarily increasing the rotational velocity such that the pressure exerted by the second solution overcomes the capillary pressure required to deliver the solution from the reservoir to the mixing chamber;
  periodically accelerating and decelerating the platform in order to re-suspend the sedimented particles into the second fluid while insuring that the rotational velocity does not exceed a defined value, thereby resulting in a suspension of particles substantially free from the original fluid.

In one embodiment there is provided a method for detecting particles on a rotating platform comprising one or more of the following steps of:
  causing a fluid containing particles to flow through a substantially azimuthally-oriented flow channel by rotating the platform at a rate such that the velocity of the central streamline multiplied by the period of rotation divided by the length of the channel is less than 1;
  providing illumination at the radial position of the flow channel;
  defining the size of the illuminating spot to be less than 100 um in the azimuthal direction and greater than or equal to the width of the flow channel in the transverse direction; and
  detecting either scattered or fluorescent radiation emitted by particles within the flow channel, passing through the illumination spot.

In one embodiment there is provided a method for washing and then detecting particles comprising one or more of the following steps of:
  configuring a platform adapted to provide at least one particle-washing reservoir and one flow channel for receiving washed particles;
  providing a mixture of particles and solution within the washing reservoir in a defined volume;

rotating the platform at a first rotational velocity for time sufficient to sediment the particles against the distal wall of the washing reservoir;

increasing the rotational velocity such that the pressure exceeds the capillary pressure required to deliver fluid through the waste channel to the first waste reservoir, thereby draining all fluid except for a defined amount containing the sedimented particles, into the waste reservoir;

adding a second volume of fluid greater than the initial volume of the particles in solution;

periodically accelerating and decelerating the platform in order to resuspend the sedimented particles into the second fluid while insuring that the rotational velocity does not exceed a defined value, thereby resulting in a suspension of particles substantially free from the original fluid;

rotating the platform at a velocity greater than the first defined value, such that the pressure exceeds the capillary pressure required to deliver fluid through the flow the channel to the second waste reservoir;

adjusting the rotational rate such that the velocity of the central streamline multiplied by the period of rotation divided by the length of the channel;

providing illumination at the radial position of the flow channel;

defining the size of the illuminating spot to be less than 100 um in the azimuthal direction and greater than or equal to the width of the flow channel in the transverse direction; and detecting either scattered or fluorescent radiation emitted by particles within the flow channel, passing through the illumination spot.

In one embodiment there is provided a platform adapted to be coupled to a rotary motor, said platform comprising:

at least one particle-washing structure and particle receiving structure adapted for receiving particles washed in the particle washing structure; and a detection zone for detection of washed particles in the particle receiving structure while the platform rotates.

In a further embodiment there is provided a method for processing biological samples comprising:

coupling a platform to a rotary motor;

configuring the platform with at least one particle-washing structure and particle receiving structure;

receiving particles in the particle receiving structure washed in the particle washing structure; and detecting washed particles in the particle receiving structure while the platform rotates, wherein the particles are immuno-modified beads and/or fluorescently labelled immuno-modified beads representative of characteristics of said biological sample.

BRIEF DESCRIPTION OF THE DRAWINGS

The invention will be more clearly understood from the following description of an embodiment thereof, given by way of example only, with reference to the accompanying drawings, in which:—

FIGS. 5*a*-5*c* illustrates the fluidic processes of the wash of FIG. 4;

DETAILED DESCRIPTION OF THE INVENTION

Figure 1:
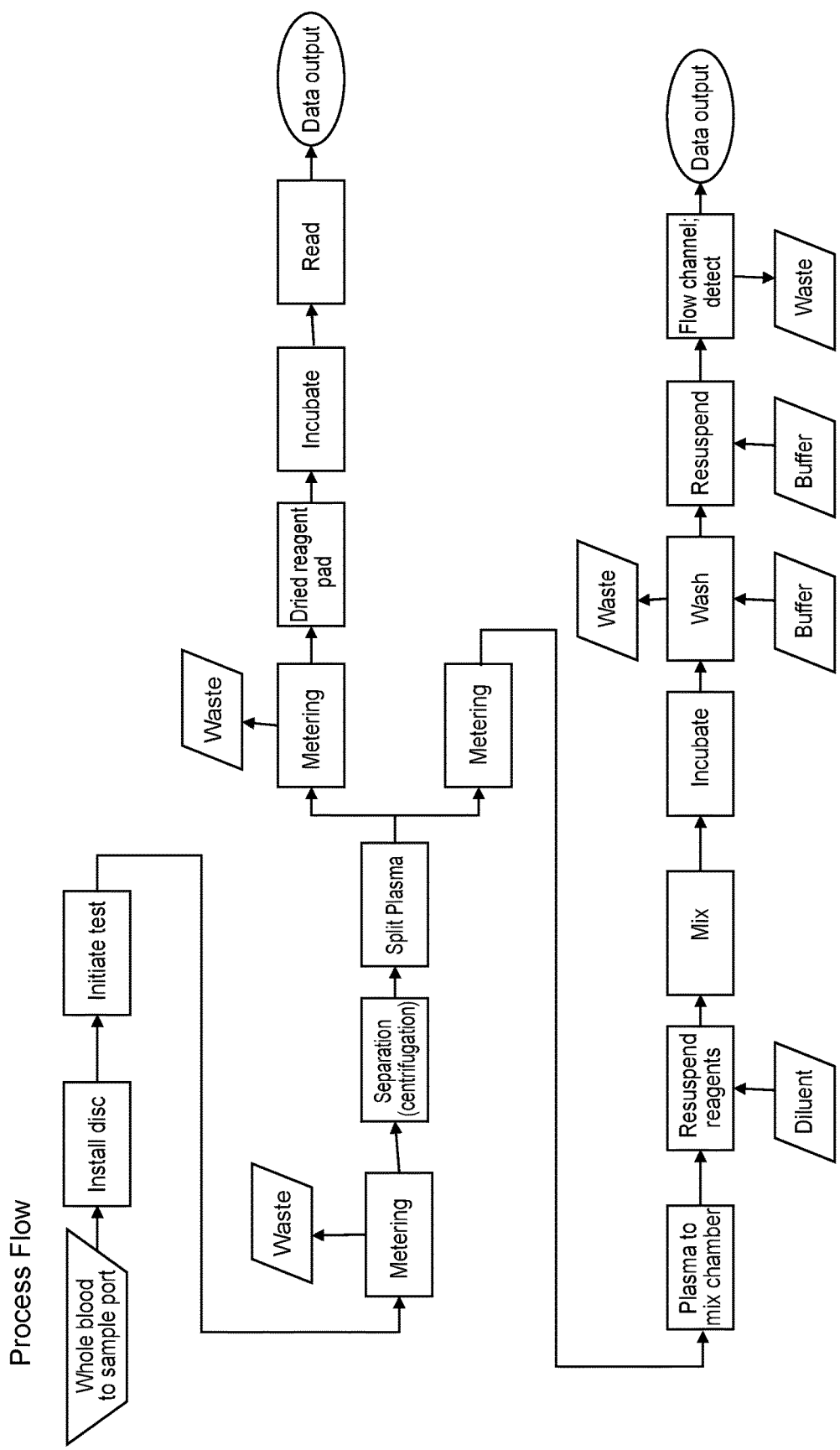
FIG. 1 illustrates an exemplary process flow a device performing an immunoassay and clinical chemistry assay on a centrifugal microfluidic disc.

An exemplary process flow for a device performing an immunoassay and clinical chemistry assay on a centrifugal microfluidic disc is illustrated in FIG. 1. These processes are divided between those performed by the user and those performed by the disposable, reagent, and instrument system. The user processes are:

Applying whole blood to the device. This may be done from a heparanized sampling device or from a finger-prick directly into a port containing anticoagulant.

Installing the microfluidic device into the instrument. The user may also seal the entry port to prevent generation of aerosols, etc.

Initiating testing process.

The processes carried out by the system are then completely automated, consisting of:

Metering whole blood.

Plasma separation

Splitting and metering plasma aliquots for the immunoassay processing channel and the clinical chemistry processing channel.

It is recognized that while a single immunoassay and single clinical chemistry processing channel are illustrated, there may be many more assays, limited only by the size of the sample and size of the microfluidic disc.

The processes in the clinical chemistry channel consist of
An additional metering step as necessary, to further define the plasma volume for the clinical chemistry
delivery of the plasma to a dried reagent pad device embedded within the microfluidic disc
incubation of plasma on the pad, to allow color generation
o generation of fluorescent product
detection The processes in the immunoassay channel consist of
An additional metering step as necessary, to further define the plasma volume for the clinical chemistry
Delivery of plasma to a mixing chamber. This mixing chamber may contain dried reagents, such as immuno-modified beads and fluorescently-labeled antibodies which engage in competitive or sandwich assays with the analyte and bead substrate. It is recognized that the reagents may also be stored in a liquid state and delivered to the mixing chamber
Mixing of sample and reagents. This can occur in a number of ways detailed below, including a) agitation, b) reciprocation, c) co-injection
incubation of mixture at sufficient temperature and for sufficient time to ensure a complete immunochemical reaction
washing of the beads to remove unbound fluorescent labels. in some cases washing can be replaced by sedimentation of beads, removal of supernatant, and resuspension and dilution of the beads (and remaining unincorporated label) by buffer
injection of beads into the flow channel for detection Fluidic Processes on Centrifugal Platforms Three fundamental functions enable most disc-based processes:
Pumping of fluids through channels by rotation of a disc of specific design at pre-defined rotation rates
Valving using passive means
Separations based on density differences and centrifugal force, e.g., plasma separation, sedimentation of beads A detailed description of these processes is provided below. Specific design considerations—both geometric design of the microfluidic disc and rotation profile—are described which enable implementation of the overall sample processing steps detailed above.

Pumping

Generating flow—with or without the use of sheath fluids—can be readily accomplished in a centrifugal format. For a substantially straight channel, the fundamental equation relating flow rate Q to geometric, fluid, and operational parameters in the laminar regime (Reynolds number <~2200) is $$Q = \frac{A d_H^2 \rho \omega_R^2 \Delta R \bar{R}}{32 \eta L}.$$ Equation 1

In this equation, Q is the flow rate. The geometrical parameters are A=the cross-sectional area of the channel=h×w, where h and w are the depth and width of a rectangular channel; $d_H$ is the hydraulic diameter, defined as 4 times the cross-sectional area divided by the perimeter of the channel; OR is the "head height" of the fluid, defined as the difference in radial position between the inner meniscus of the fluid at $R_0$ and outer meniscus at $R_1$, $\Delta R = R_1 - R_0$; $\bar{R}$ is the average position of the liquid, $\bar{R} = 0.5(R_1 + R_0)$; and L is the length of the channel. The fluid parameters are $\rho$=the density of the fluid and $\eta$=the kinematic viscosity of the fluid. Finally, the operational parameter is the angular velocity $\omega_R = 2\pi f_R$, where $f_R$ is the number of revolutions per second, which itself will be a function of time for the rotational profile required. This expression is accurate for flow rates with Reynolds numbers <2200 (laminar flow).

From Equation 1 the average velocity $\bar{u}$ is $$\bar{u} = \frac{Q}{A} = \frac{d_H^2 \rho \omega_R^2 \Delta R \bar{R}}{32 \eta L}$$

The maximum velocity—that experienced by fluid at the centre of the channel—is $2\bar{u}$. In some applications this velocity is the relevant parameter, i.e., in terms of insuring that each particle in a flow channel is detected at least once per rotation.

Valving

There exist a variety of means for gating or valving liquids in a centrifugal fluidic platform, including but not limited to the use of siphoning; passive single-use valves based on surface tension effects (capillary valves, hydrophobic valves); single-use valves based on solid-to-liquid phase transition or melting of a "plug" due to heat applied by a contact heater or light source; and multiple-use valves based on the same principals.

Some of these valving mechanisms are well known in the art and have entered the public domain, such as siphons.

Passive 'capillary' valving is particularly useful and has been shown to be valuable for nearly all fluids tested. In capillary valving, surface or capillary forces act to retain fluids at changes in cross-section of a channel. For liquid/solid contact angles greater than 0-degrees, emergence from a narrow channel into a larger channel, especially across a junction with a discontinuity, requires the creation of a positive radius of curvature of the liquid-vapour interface through application of a pressure differential across the interface, with the pressure higher on the liquid side. This pressure may be generated through rotation of the microfluidic disc. In general, the pressure required to generate flow across the interface for hydrophilic surfaces is directly proportional to the surface tension of the fluid and the cosine of the contact angle, and inversely proportional to the diameter of the capillary. Useful and readily fabricated dimensions of capillary valves are 50-500 um wide×50-500 um deep channel segments, typically intersecting a deeper channel or pocket.

Fluid is retained at the capillary junction if the hydrostatic pressure due to rotation is less than this capillary pressure. On a rotating platform, this hydrostatic pressure is directly proportional to the average position of the fluid (measured between the leading and trailing menisci, or radially outward and inward menisci of the liquid volume); the difference in the positions of the menisci; and the rotational frequency squared.

It is recognized in the art that manipulation of liquid properties (surface tension, density), material properties (contact angle); and geometric parameters such as the capillary dimensions and configuration of the fluids on the disc; results in well-defined rotational velocities at which capillary pressure is 'defeated' and liquid 'bursts' through passive valves. Using these relationships, a wide range of relevant biological fluids and reagents may be gated at rotational rates from a few hundred RPM (revolutions per minute) to more than 5000 RPM. These relationships can be summarized in the following equation:

$$RPM_C = \frac{60\omega_c}{2\pi} \approx \frac{30}{\pi}\left[\frac{\gamma \sin\theta_C}{\rho \bar{R} \Delta R d_H}\right]^{1/2}$$

where RPMc is the critical RPM, below which fluid does not flow through the capillary valve and above which it does; $\gamma$ is the liquid surface tension; $\theta_C$ is the contact angle of the liquid on the material of the disc; $\bar{R}$, $\Delta R$, $d_H$ and $\rho$ are defined as above.

Separations Based on Density Differences and Centrifugal Force

Inherent in the centrifugal platform is the ability to separate fluids based on density differences between components under the application of centrifugal force. For spherical particles, a useful expression for the velocity which particles "sediment" is $$V_s = 5.448 \times 10^{-5} \cdot (\rho_P - \rho_L) \times (\eta_W \eta_L) \times d^2 \times acc$$

Here, $V_S$ is the particle velocity in cm/sec; $\rho_p$ is the particle density; $\rho_L$ is the liquid density; $\eta_W$ is the kinematic viscosity of water; $\eta_L$ is the kinematic viscosity of the liquid; d is the particle diameter in microns; and acc is the acceleration in gravities (982 cm/sec$^2$=9.82 m/sec$^2$=1 gravity).

Mixing

A variety of methods are possible for mixing fluids on a centrifugal disc. First, agitation may be employed, in which the liquids to be mixed, or liquid and solid to be solubilised, are placed in a chamber with included air. Alternating acceleration and deceleration provide mixing action. This method is employed in the embodiments and example below.

A further mixing means is reciprocation of fluid against trapped air. In this method the fluid mixing chamber is connected by a narrow channel to a trapped air volume "ballast" which has no venting port. As a result, at low rotation rate the fluid is stopped by the trapped air. As the rotation rate is increased, the fluid intrudes into the trapped air volume, compressing the air in response to the centrifugally-generated pressure due to the fluid. Reducing the rotation rate leads to retraction of the fluid from the ballast chamber. In this way, alternating high rotation rate/low rotation rate cycles provide reciprocating motion analogous to "pipette" mixing.

Finally, mixing may be done by injecting the two fluids to be mixed into a channel from reservoirs, for example, by bringing the fluids to capillary valves on opposite sides of the channel. The fluid is then deposited in a receiving reservoir. If the amount of time the two co-flowing solutions are present in the channel is sufficient, diffusional mixing of the fluids takes place. If not, turbulent motion upon entry into the receiving reservoir effectively mix the fluids.

Detection Requirements—Immunoassay Detection: Rotating Flow Channel

In traditional flow cytometers, sheath flow is used to dilute the particles to be measured and place them "single file" in the center of a channel, where they are interrogated by the light source of the instrument. This is done with an optical detection volume which is narrow, typically 10 um, in the flow direction; but much broader than the "core" of the sheath flow in the transverse direction. Sheath flow has the dual functions of placing the particles in a substantially homogeneous radiation field from the light source, thereby minimizing variations in detected radiation due to the light source; as well as diluting the particles, so that only a single particle at a time is illuminated by the light source.

For immunoassay applications, the bead concentration may be established such that further dilution is not required. For example, a concentration of 200 particles in 10 uL—a typical immunoassay concentration—flowing through a channel 250 um square, results in a mean particle-particle spacing of 800 um. As a result, the probability of counting more than one particle at a time is vanishingly small. By using a beam which traverses the entire flow channel and is substantially uniform, all particles may be counted without simultaneous detection and without significant variations induced by the light source. This obviates the need for a sheath flow.

In detecting moving particles on a rotating disc while using a stationary detector, it is important that the sampling rate of the detection system is adequate to detect particles. Since the velocity is dominated by the disc velocity at radius $R_F$, radius of the flow channel, the total number of samples is simply related to the width of the detection volume in the azimuthal (rotation) direction of the disc (here wl), velocity=$\omega R$, and sampling rate in Hz $f_S$:

$$N_S = \frac{w_l}{\omega R_F} \times f_S$$

Using $f_S=10^6$, $w_l=80$ um, and a rotation rate of 500 RPM and radial position $R_F$ of 50 mm, we find Ns~31, an adequate number for good statistical sampling.

Embodiments

Many forms of immunoassay for a centrifugal format with flowing beads as the detection step can be implemented incorporating the invention. For example in one embodiment:

1. Mix 50 uL functionalized beads (6000 beads) with 50 uL of sample and 50 uL labeling reagent (phycoerythrin, PE) (VS=150 uL)
2. Incubate 3 hours
3. Add 1000 uL wash buffer (VW)
4. Centrifuge to pellet beads
5. Discard supernatant
6. Resuspend in 300 uL of buffer (VE)
7. Perform flow cytometry Fundamentally, bead washing is removal of excess of unincorporated dye (PE) to a level where it does not interfere with detection of bead fluorescence (i.e., the background is low relative to the bead fluorescence).

Embodiments of Washing

Preferred embodiments of washing include:

Pellet+decant+dilute: Centrifugation to pellet beads; remove (decant) supernatant, leaving behind a residual amount of solution; and resuspension of beads in buffer to achieve sufficient reduction of concentration of residual materials Wash by pelleting: As above, but with a second pelleting of beads and removal of supernatant, followed by resuspension of the beads in buffer. This may be repeated.

Filtration with filters: The solution containing beads is driven against a filtering element and the beads are washed.

Filtration with traps: The solution containing beads is driven against traps formed in the substrate of the disc, such as channels of dimensions smaller than those of the beads or weirs (channels confined in one dimension but bigger in the transverse dimension). This traps the beads and allows washing.

In all cases, waste must be directed to one or more reservoirs, prior to resuspension and injection of the beads into a detection structure, such as a flow channel or pelleting chamber as described in more detail below.

Pellet+decant+dilute. This process essentially miniaturizes the laboratory-scale process described in the protocol due to Becton Dickinson (BD) above. In the BD process, sample is initially diluted by wash and then excess wash removed. Resuspending in buffer results in an overall lower concentration of soluble constituents of the first solution, while the number of beads is conserved.

As an alternative, the current invention sediments the beads first, and decants the supernatant, followed by re-suspension in a volume of buffer.

The disc-based process can be implemented by:
1. Start with sample volume VS
2. Sediment the beads through centrifugation
3. Discard a volume VS-VRR of supernatant
4. Add a volume VE>VS of elution/wash buffer and resuspend the beads through gentle agitation
5. Perform flow cytometry This results in a dilution factor DFC of the original reagents is then $$DFC = \left(\frac{VRR}{VE + VRR}\right)$$

Proper choice of VRR, VE ensures that this dilution factor is equal to or lower than that required for detection of the beads against the background of remaining contaminants.

Figure 2:
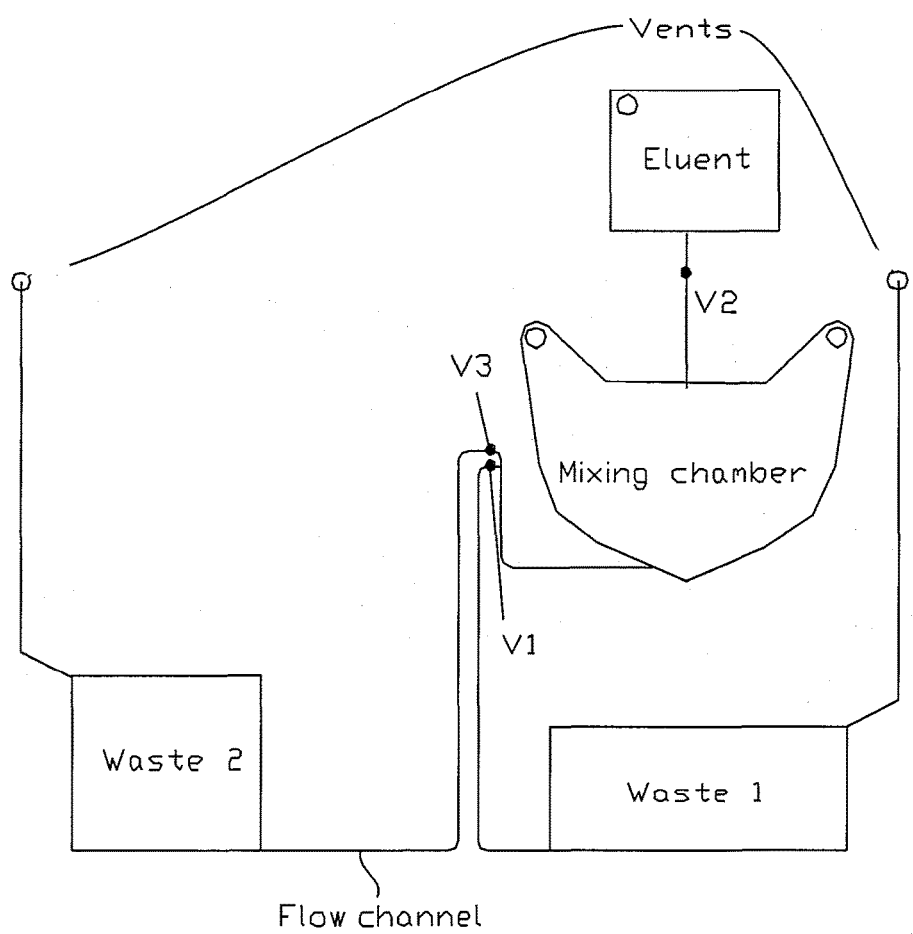
FIG. 2 illustrates schematically a disc structure which provides a dilution or wash process followed by injection of beads into a flow channel.

FIG. 2 illustrates schematically a disc structure which provides this dilution or wash process followed by injection of beads into a flow channel. It is understood that other disc structures not shown are used for preparation of the sample (e.g., plasma separation) and delivery of liquid reagents and sample to the mixing chamber which is shown. In mixing chamber the beads, sample, and reagents are incubated and are present in solution at the beginning of the wash process. Two waste chambers are connected to this. Waste 1 has a volume approximately equal to the volume of solution to be applied to the mixing chamber and is connected to the mixing chamber via capillary valve V1. Waste 2 receives the bead-containing "injection' that is detected in the flow channel and is connected by a capillary valve V3. Additionally an eluent chamber is connected to the mixing chamber by capillary valve V2.

Figure 3A:
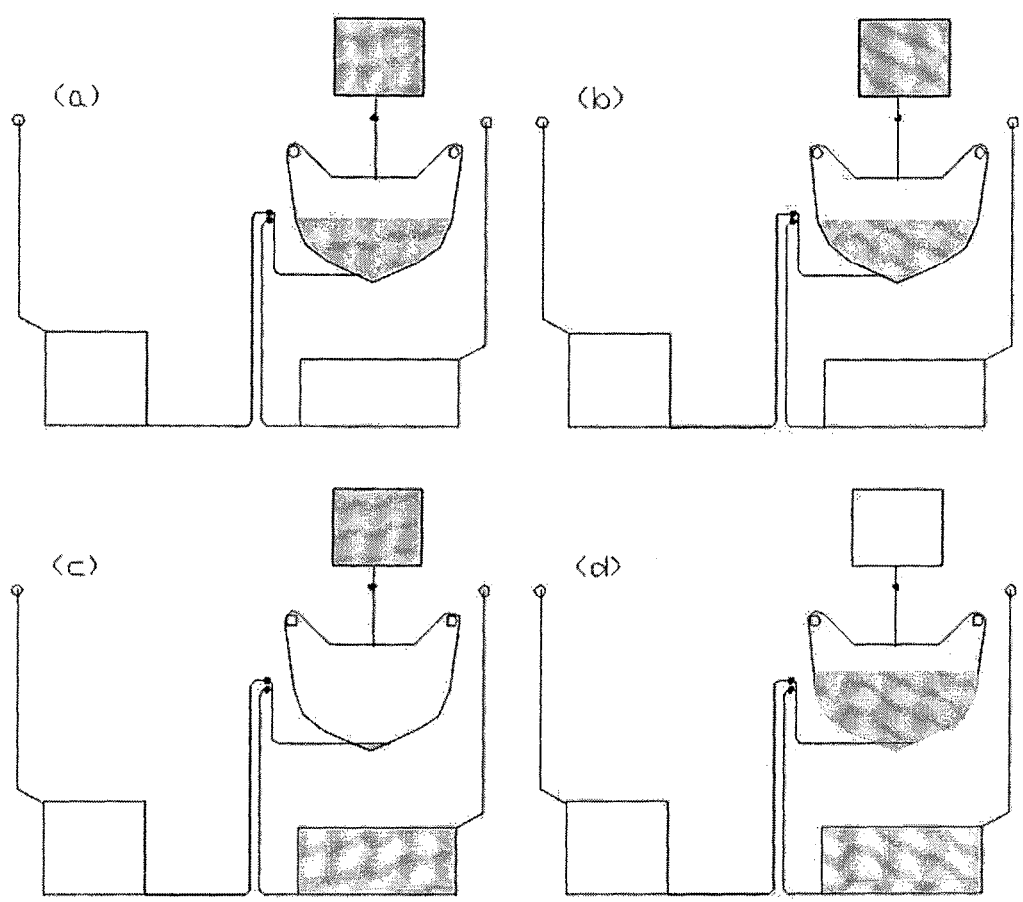
FIGS. 3*a*-3*b* illustrates the fluidic processes of the wash of FIG. 2.
Figure 3B:
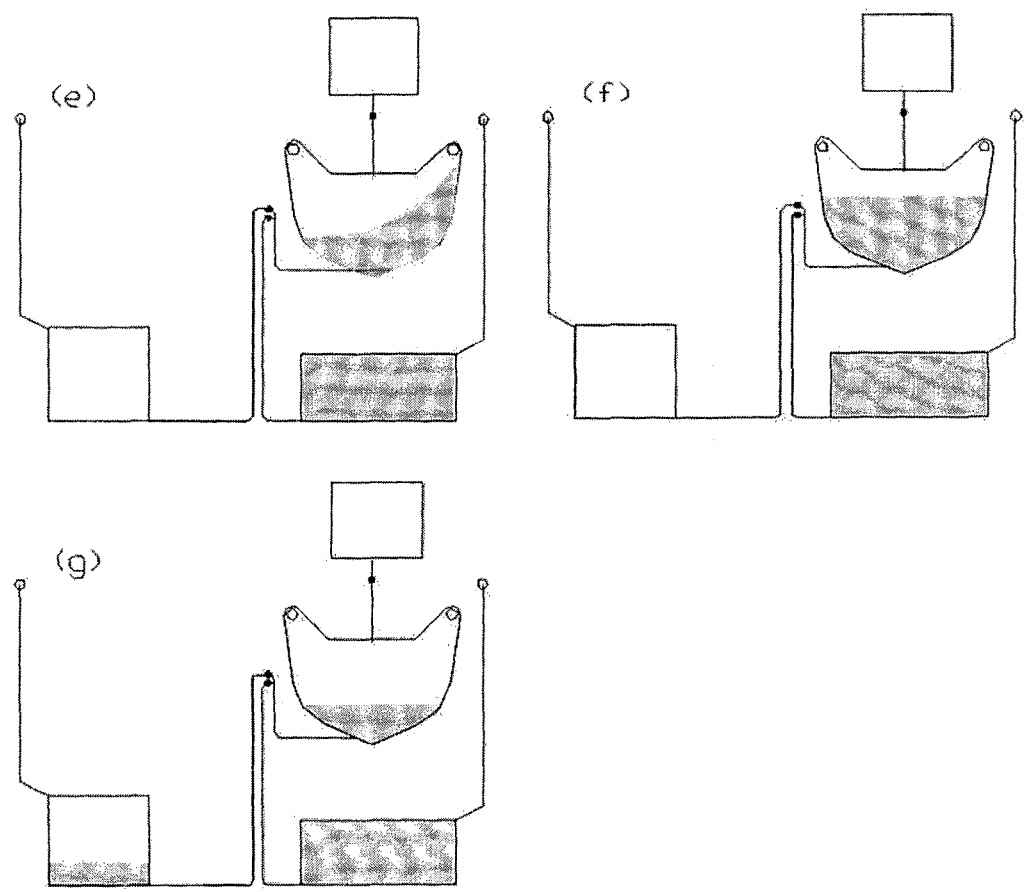

FIGS. 3a-3b illustrates the fluidic processes of this wash:
a. Sample volume VS added to mixing chamber. The solution may contain beads or may be a sample which rehydrates beads and reagents present in the mixing chamber. If necessary, the system is then agitated by acceleration and deceleration to mix the beads and liquid.
b. A high-speed spin at frequency W1 is used to sediment beads.
c. The rotation rate is increased to W2>W1. This defeats a capillary valve V1 in the output of the mixing chamber and decants solution that is radially-inward of the point where the channel joins the mixing chamber into the first waste reservoir. In this embodiment, the radial position of the inner meniscus for the designed volume VS is radially outward of the position of valve V3; as a result, valve V3 may not be defeated by the initial sample at any rotational rate. The velocity may be reduced to a value below W2 after valve V1 is defeated The retained fluid VRR is defined as that radially-outward from the channel. As this fluid flow is slow and does not significantly disturb the fluid near the outer wall, the beads sedimented in the previous step remain at the outermost surface of the mixing chamber. The first waste chamber is defined to have a size approximately equal to the volume of liquid removed from the mixing chamber, VS-VRR. Furthermore, the air exhaust channel from the first waste chamber terminates in a port or joins a channel radially-inward of any contemplated fluid meniscus position under uniform rotational velocity.
d. Rotation is spiked to W3>W2 to deliver a volume of elution buffer to the mixing chamber by defeating capillary valve V2. Slowing rotation before the full volume is delivered insures that hydrostatic pressure sufficient to defeat capillary valve V3 is not exerted.
e. The elution fluid re-suspends the beads through gentle agitation at low RPM.
f. Rotation is spiked to W4 to defeat capillary valve V3 leading to the flow channel and rapidly slowed to prevent sedimentation of the beads. This carries bead-containing solution through the flow channel to Waste 2, because Waste 1 is filled with fluid; additionally, the venting channel from Waste 1 may fill with waste fluid and provide a countering pressure to that generated by the elution buffer as it flows into the flow channel, ensuring that the bead-containing injection does not enter Waste 1. As necessary there may be additional agitation steps as the sample flows, to ensure that the concentration of beads in the mixing chamber remains homogeneous.

Wash by Pelleting:

A preferred method is to perform a true multi-step wash, using the following steps
1. Start with sample volume VS
2. Sediment the beads through centrifugation
3. Discard a volume VS-VRR1 of supernatant, where VRR1 reasonably large (e.g., 0.2VS), leaving behind VRR1
4. Add a volume VW of wash buffer, creating total volume VW+VRR1, and resuspend the beads through gentle agitation
5. Sediment the beads through centrifugation
6. Discard a volume VW+VRR1−VRR2 of the dilute solution, leaving behind VRR2.
7. Add a volume VE of elution/wash buffer, creating a total volume of VE+VRR2, and re-suspend the beads through gentle agitation.
8. Perform flow cytometry or detect beads The dilution factor in this case is $$DFC = \frac{(VRR1)(VRR2)}{(VW + VRR1)(VE + VR2)}$$

Figure 4:
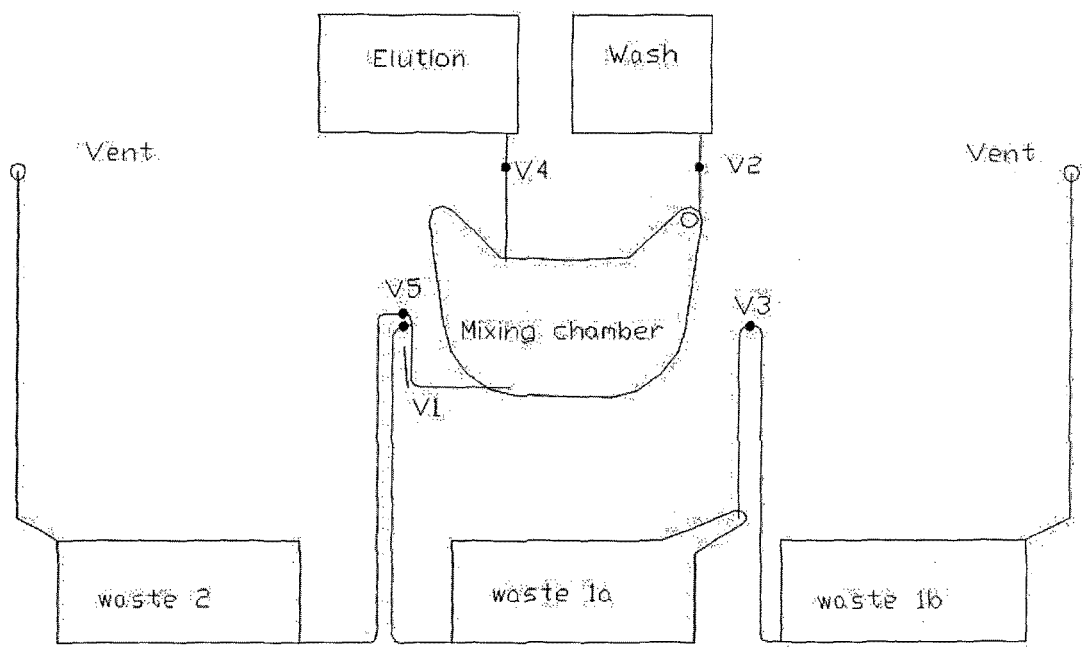
FIG. 4 illustrates schematically a disc structure which provides an alternative dilution or wash process followed by injection of beads into a flow channel.
Figure 5A:
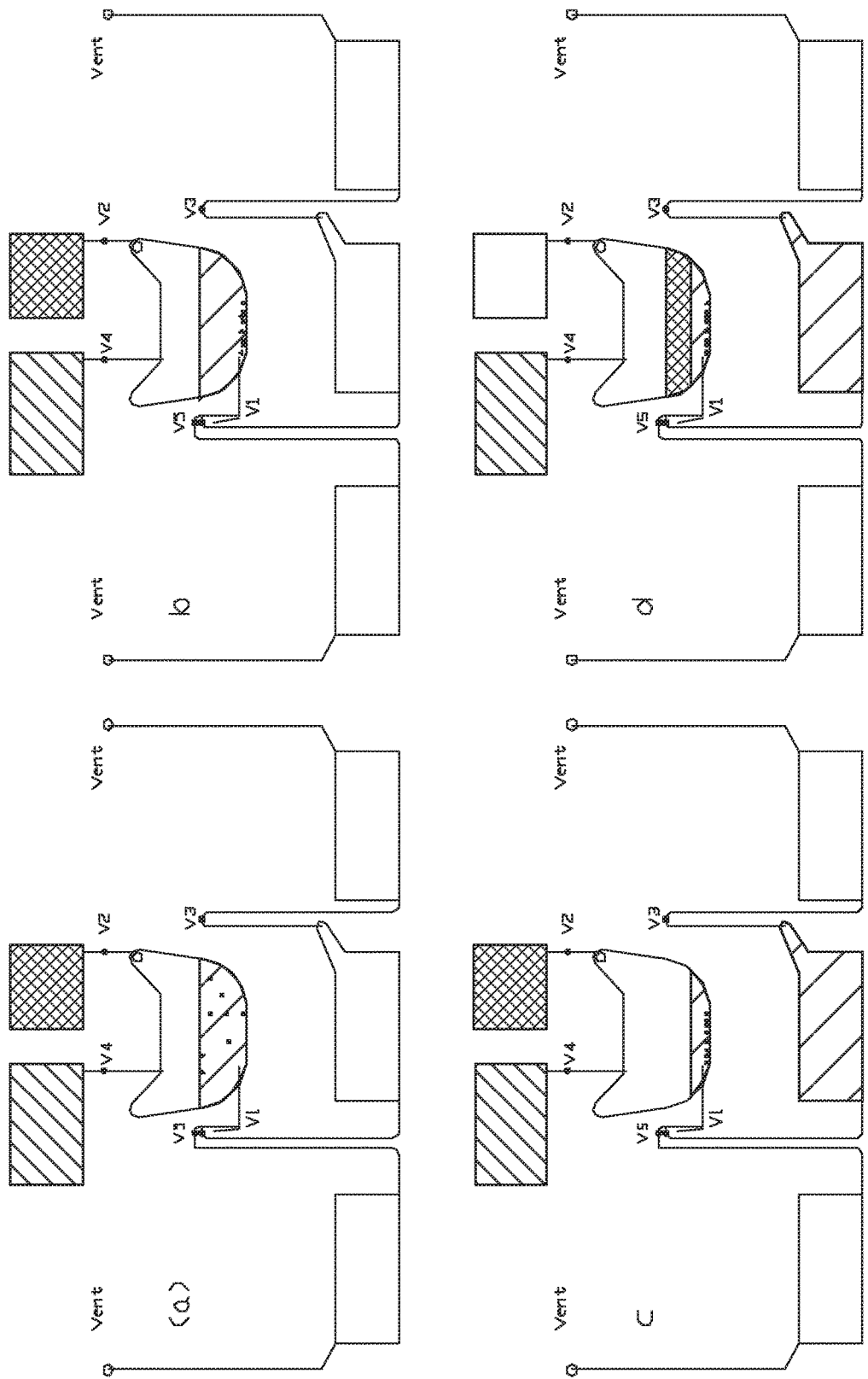
Figure 5C:
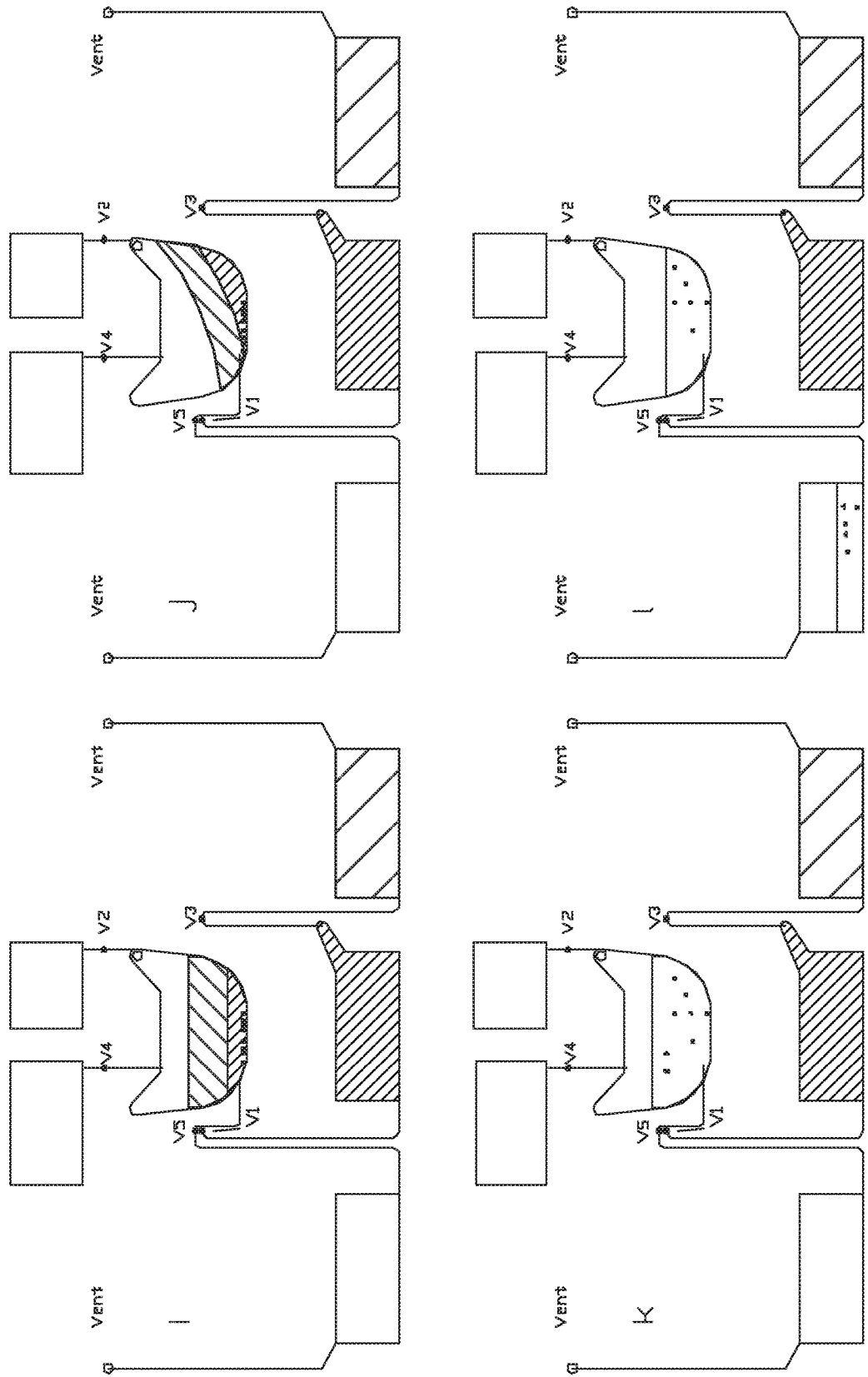

FIG. 4 illustrates schematically a disc structure which provides this dilution or wash process followed by injection of beads into a flow channel. It consists of a mixing chamber in which beads to be incubated and washed are placed in solution. Two serial waste chambers are connected to this. Waste 1a has a volume that is approximately equal to the volume of solution to be applied to the mixing chamber and is connected to the mixing chamber via capillary valve V1. The second serially connected waste chamber Waste 1b is connected to the outlet of the first via capillary valve V3 and has a volume somewhat less than the initial sample volume—waste 1a+a wash buffer volume, the wash buffer initially held in the wash chamber. This wash chamber is connected to the mixing chamber by valve V2: A third waste chamber, Waste 2 receives the bead-containing "injection' that is detected in the flow channel and is connected by a capillary valve V5 to the waste chamber. Additionally an eluent chamber is connected to the mixing chamber by capillary valve V4.

FIGS. 5a-5d illustrates the fluidic processes of this wash:
a. Sample volume VS added to mixing chamber. The solution may contain beads or may be a sample which rehydrates beads and reagents present in the mixing chamber. If necessary, the system is then agitated by acceleration and deceleration to mix the beads and liquid.
b. A high-speed spin at frequency W1 is used to sediment beads.
c. The rotation rate is increased to W2>W1. This defeats a capillary valve V1 in the output of the mixing chamber and decants solution into waste reservoir Waste 1a. The solution flows until stopped by valve V3 in the output of Waste 1, leaving behind a volume VRR1. The radial position of the meniscus of sample is outward of that of V4, insuring that valve V4 is not defeated by the sample volume VS during this process.
d. Rotation is spiked to W3>W2 to deliver a volume of wash buffer to the mixing chamber by defeating capillary valve V2.
e. The wash buffer fluid resuspends the beads through gentle agitation at low RPM.
f. As shown, the beads are resuspended
g. Rotation is increased to W1 to sediment the particles once more in this mixed solution
h. Rotation is spiked to W4 to defeat capillary valve V3 connecting Waste 1a with Waste 1b. The mixed wash and residual initial sample solution are decanted, passing first through Waste 1a and then into Waste 2a. A volume VRR2=VRR1+VWASH−VWASTE 1b is retained within the mixing chamber
i. Rotation is spiked to W5 to defeat capillary valve V4 connecting elution buffer to the mixing chamber and elution buffer is delivered.
j. Gentle agitation resuspends the particles.
k-l. Rotation is spiked to W6 to defeat capillary valve V6 connecting the mixing chamber to the flow channel and rapidly slowed to prevent sedimentation of the beads. This carries bead-containing solution through the flow channel to Waste 2, because Waste 1 is filled with fluid. As necessary there may be additional agitation steps as the sample flows, to ensure that the concentration of beads in the mixing chamber remains homogeneous.

These two examples are in no way limiting of concepts which combine the use of capillary valves, siphons, and pelleting to effect washing.

Embedded Filters can be incorporated readily into microfluidic devices and typically are used in the same way as the same materials are used in more conventional products. Some applications are filtration products to remove particulates; filters for trapping particles for further use; hydrophobic vent filters; or as solid phase binding supports for SPE.

Many filter materials are available and material choice depends on application. Bonding methods for insertion include press-fit, O-rings, adhesives, and thermal bonding (hot melt bonding). Methods are dependent upon filter choice: silica membranes are fragile and often held into devices using compression by press-fit members; polypropylene filters would be inappropriate in a thermally-bonded cyclic olefin (cyclic olefin polymer [COP] or cyclic olefin copolymer [COP]) part that must be heated to 138° C. for bonding. Examples in the "macro" world include filter-based products from Millipore and Pall. Frits can be used to provide mechanical support to filter media of interest.

Filters present additional manufacturing complications but these are not insurmountable. Filters must be formed (e.g., die-cut) and placed (e.g., by automated machinery) and potentially tacked in place prior to final bonding. In prototyping this is relatively straightforward; in large-scale manufacture, filters would be typically cut and then placed using pick-and-place automation. Millipore performs large-scale "hot plate" welding of filter units.

A small filter of appropriate pore size—such as 0.4 um PES (polyethersulfone) filters, commonly used for laboratory filtration—is bonded between the mixing chamber and the channel leading to the waste chamber. As a result, fluid must pass from one component of a disc to another structured component ("lid" to "bottom" with an interlayer required for leak-proof bonding). An advantage of this approach is that it readily allows concentration of the sample during the washing step: The volume of sample applied may be more than the volume of elution buffer. It also relaxes the requirements in terms of rotation rates and geometry, since sedimenting the particles is not required.

Figure 6:
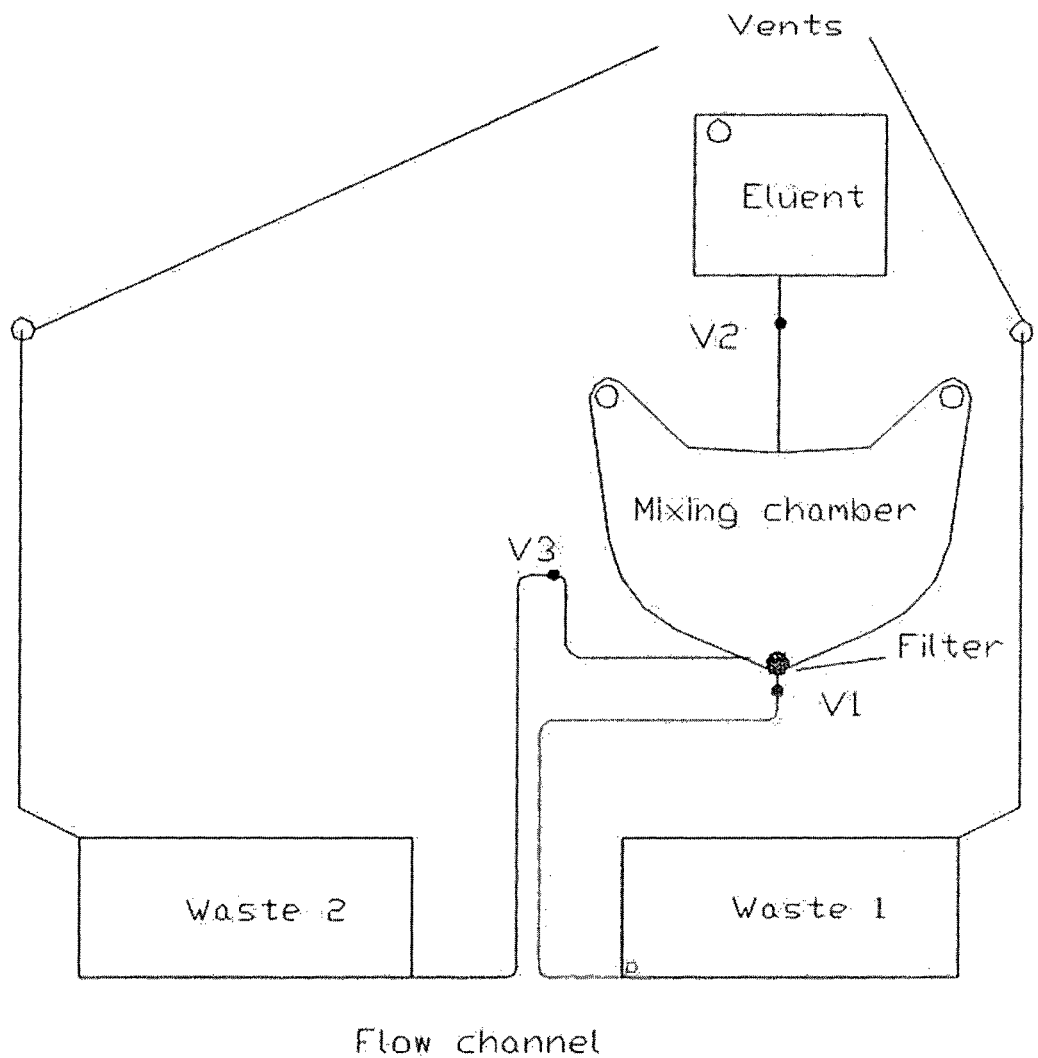
FIG. 6 illustrates a disc-based structure using a filter for washing of particles.

FIG. 6 illustrates a disc-based structure using a filter for washing of particles. The disc is composed of 2 or 3 layers. The majority of the structures are on the main layer shown in black. The filter is bonded between this layer and a second layer consisting of a single channel. Additionally it is sometimes useful to use an intermediate layer consisting of through-holes where the upper and lower layer connect; the through hole in the filter region ensures that a leak-proof "ring" is formed around the filter. The features on this disc include a mixing chamber in the first layer which beads to be incubated and washed are placed in solution. A waste chamber Waste 1 is connected to the mixing chamber by a channel in the second layer that terminates at Waste 1 and is positioned beneath the embedded filter. Capillary valve V1 is used to resist flow into this channel and Waste 1 at low rotation rates. Waste 1 is sized to be approximately the same volume as the applied sample. There is also an eluent/buffer reservoir connected to the mixing chamber by valve V2. A second waste chamber, Waste 2 receives the bead-containing "injection' that is detected in the flow channel and is connected by a capillary valve V3 to the waste chamber.

Figure 7A:
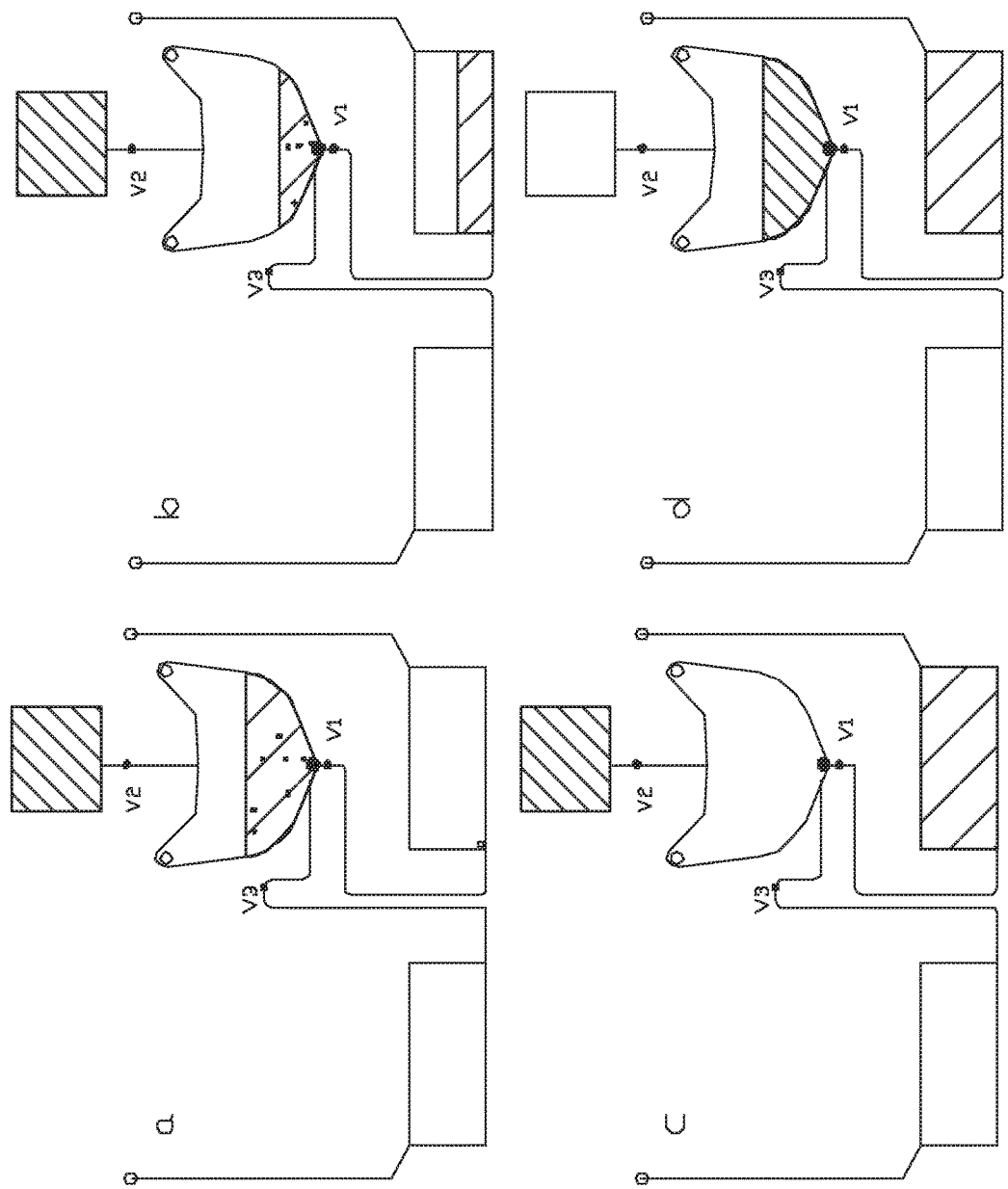
FIGS. 7*a*-7*b* illustrates the fluidic processes of this wash and injection into the flow channel of FIG. 6.
Figure 7B:
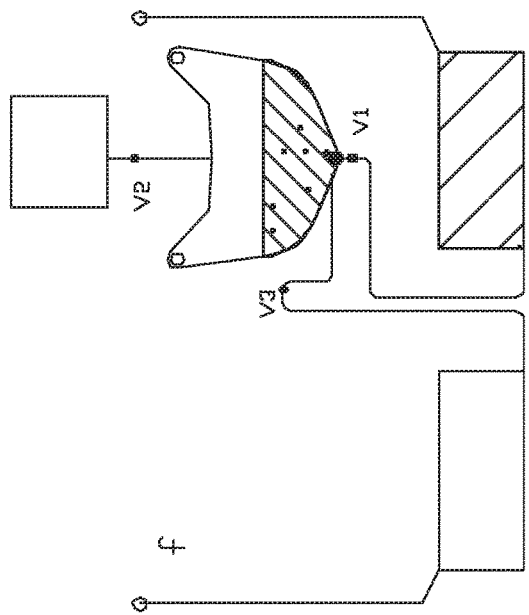
Figure 7B:
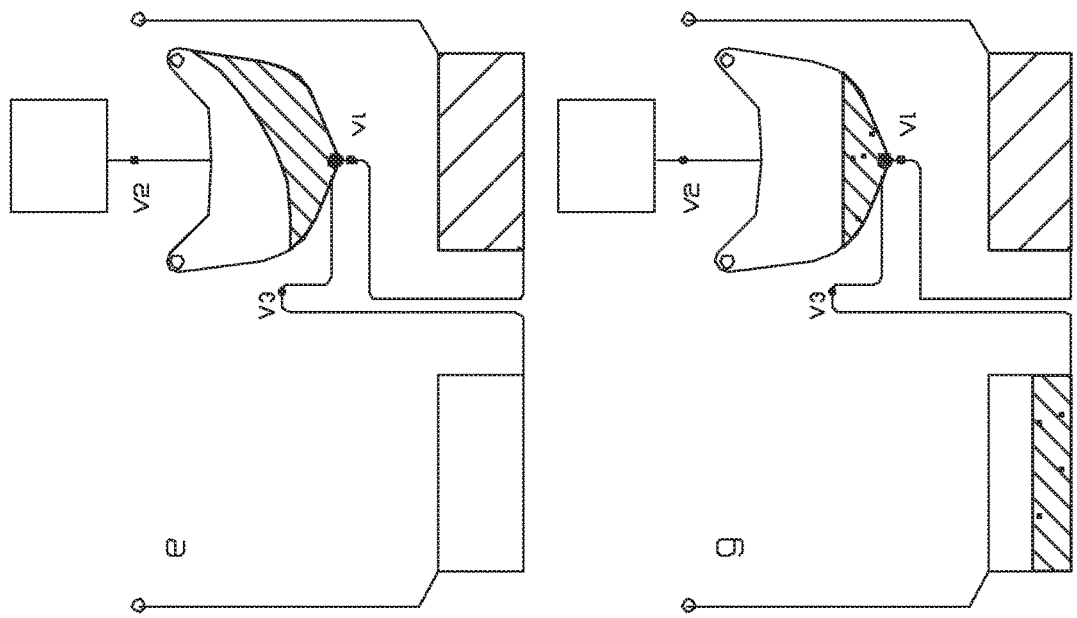

FIGS. 7a-7b illustrate the fluidic processes of this wash and injection into the flow channel
a. Sample volume VS added to mixing chamber. The solution may contain beads or may be a sample which rehydrates beads and reagents present in the mixing chamber. If necessary, the system is then agitated by acceleration and deceleration to mix the beads and liquid.
b. A high-speed spin at frequency W1 defeats valve V1, and the sample liquid is driven through the embedded filter into Waste 1.
c. All supernatant has been transferred to Waste 1. All particles are trapped on the surface of the filter exposed to the mixing chamber.

d. The rotation rate is momentarily increased to W2>W1. This defeats a capillary valve V2, allowing elution buffer to enter the mixing chamber.
e. Gentle agitation at low RPM is used to resuspend the particles in solution
f. Resuspended particles are now ready for detection in the flow channel
g. Rotation is spiked to W3>W2 to defeat valve V3, delivering particle-containing solution to the flow channel. Rotation is rapidly decreased to prevent sedimentation of the beads. This carries bead-containing solution through the flow channel to Waste 2. As necessary there may be additional agitation steps as the sample flows, to ensure that the concentration of beads in the mixing chamber remains homogeneous.

Channel Constrictions; Weirs and Dams.

Particles can be trapped by constricted channels, i.e., channel dimensions are less than particle diameter.

When particles are packed against a constriction, they form a packed particle bed with very small mean "channel diameter" formed by the spaces between the particles. Packing particles in a "cone" approaching a constricted channel will result in a very large impedance to flow formed by the long, tortuous fluid path leading through the packed bed to the channel.

A preferred approach is to use a weir or dam, which is a constriction in one dimension. Typically this is formed perpendicular to the plane of the microfluidic disc, for example at the end of a chamber. A 5 um gap formed between two components of the disc create such a weir and is used to trap particles of diameter greater than 5 um. It is preferable that this be relatively wide, so that the length of the packed bed—and hence length of the tortuous channels and resulting pressure drop, which acts to reduce the flow—is minimized.

Figure 8:
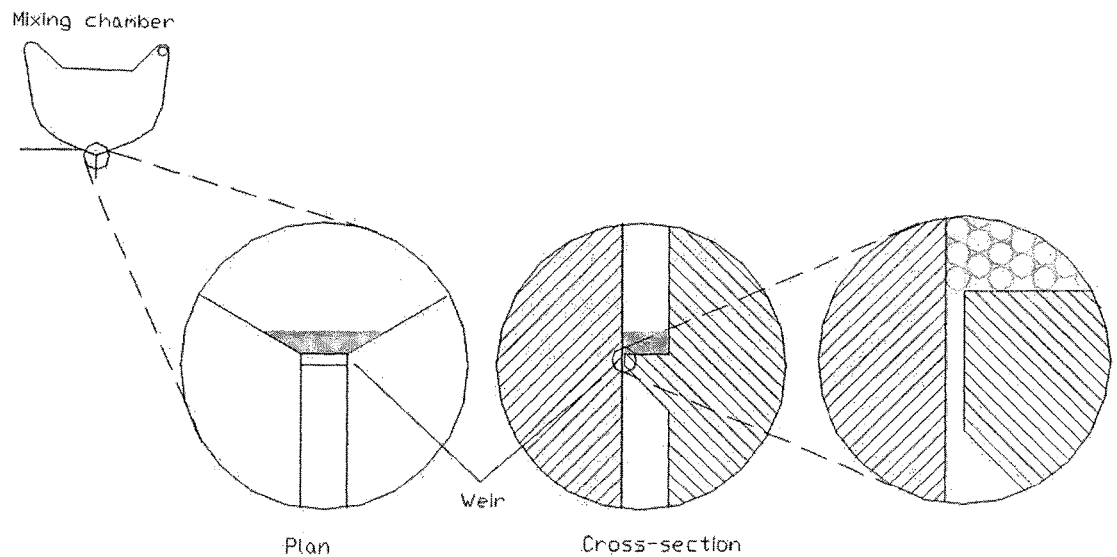
FIG. 8 illustrates layers of the invention formed with the correct geometry to provide a weir or dam.
Figure 9:
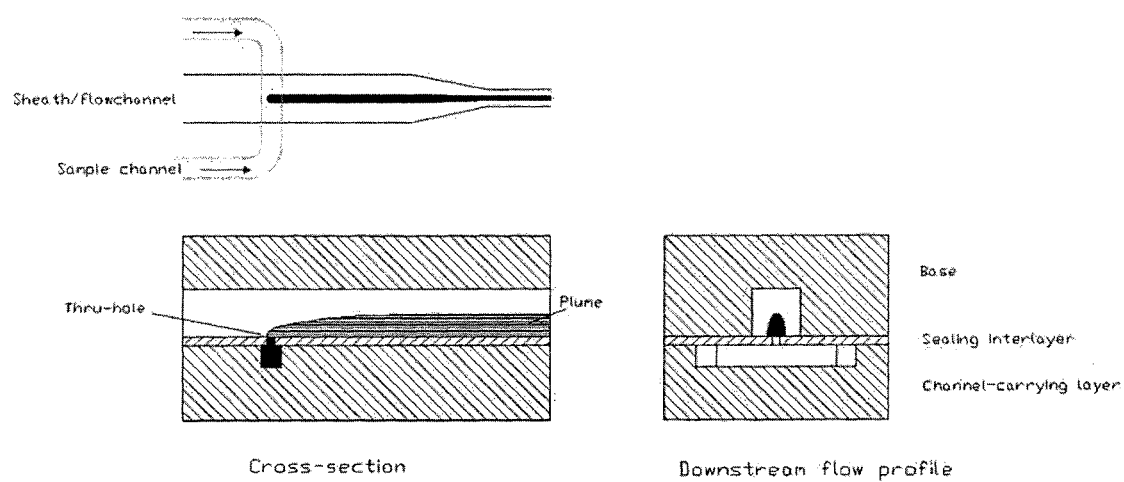
FIG. 9 illustrates a channel configuration suitable for one-dimensional sheath flow.

Microfabrication methods can be used to create such systems. Typically they are created by joining two components—for example a chamber in one layer and a "fan shaped" channel entry and channel in another layer. Bonding of layers formed with the correct geometry provides the weir. This is shown in FIG. 8.

Embodiments of Particle Receiving Structure

Preferred embodiments of a particle receiving structure include sheathless flow channels designed as described above, in which the concentration of particles is maintained at such a level as to prevent significant simultaneous detection with a excitation beam that is substantially uniform in the transverse direction (across the flow channel). The length and diameter of the channel are chosen to ensure that a relatively low rotational rate can be used while detecting each particle at least once while in the flow channel with adequate sampling time.

Flow Focusing Systems

In some applications, such as hematology applications, the discussion above shows that flow focusing may be desirable. Two ways in which such flow focusing can be provided are through sheath flow, as an extension of conventional methods, and inertial focusing Sheath Flow A variety of sheath flow implementations may be employed. The preferred methods include
Non-coaxial sheath flow.
One-dimensional sheath
Liquid rotation due to features in channel walls.
Each is treated in greater detail below
Non-Coaxial Sheath Flow.

Figure 12:
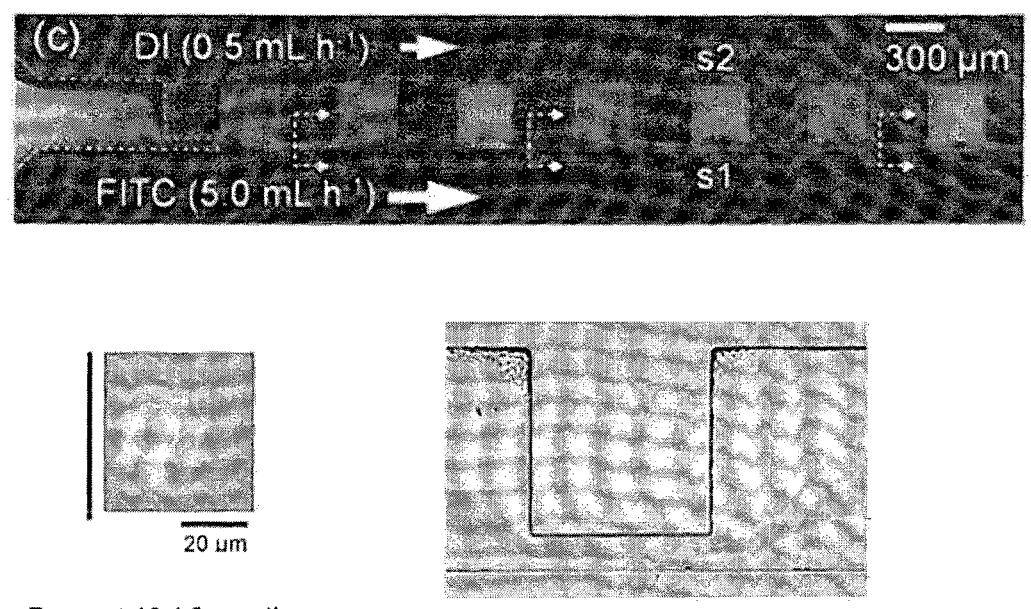
FIG. 12 illustrates an inertial focusing.

In non-coaxial sheath flow, the sample stream is injected into the sheath fluid from the channel floor. As a result, the sample stream "clings" to the channel floor and is not centered within the channel. But significant focusing occurs. The ratio of flow rates determines the degree of focusing. This is illustrated as shown in FIG. 12. Disc construction would preferably be 3 parts: base part carrying fluidics and sheath channel; sealing interlayer with small aperture or thru hole; and lower layer carrying sample to be injected through the thru hole. If the dimensions of the aperture are small, it will act as a capillary valve.

In operation, sample fluid is driven against the aperture, but does not flow through it into the main flow channel because it is retained by capillary forces, at an initial rotational rate W1. An additional acceleration to W2, with potentially a reduction in rotational rate, releases sheath fluid from an upstream reservoir. As the sheath fluid displaces air, passing through the flow channel, its meniscus eventually joins the meniscus of the retained sample fluid at the thru hole. At this point, both sheath and sample fluids flow. As is shown in the down-stream profile, the size of the sample plume in the sheath fluid can be quite small, dependent upon the relative sizes of the thru hole and flow channel width and the ratio of flow rates.

The ratio of sheath and sample flow rates can be determined by three factors: The driving "pressures" due to the radial positions of sheath and sample menisci in their reservoirs prior to their joining at the flow channel; the cross-sectional area of the sheath and sample reservoirs; and the impedances of the channels leading from these reservoirs to the junction where the sheath and sample fluids are joined. The impedances may be chosen—by varying the length and diameter of the channels—such that the ratio of the impedance of the sheath channel to the sample channel is equal to the desired ratio of sample flow to sheath flow. This means that at a given rotational rate the pressure head generated by the sheath reservoir and sample reservoir will be the same. The desired flow ratio is then achieved by ensuring:

$$\frac{Q_{sheath}}{Q_{sample}} = \frac{A_{sheath}(r)}{A_{sample}(r)}$$

Given a desired flow ratio, for each dr by which the sample's meniscus drops (moves outward in radial position), a volume $A_{sample}*dr$ flows; similarly, a volume $A_{sheath}*dr$ flows. As a result, $A_{sheath}/A_{sample}$ must=the desired sheath/sample flow ratio for all r for which the two fluids will be injected into the channel together.

As shown in the figure, the sample flow may be led to the through hole through one channel, with continuing flow inward along the radius. This achieves the desired goal of flushing trapped air from the feeding channel.

Note that further focusing in both the lateral and vertical directions can be achieved by decreasing the cross-section downstream, as shown in the Figure.

One-Dimensional Sheath.

One-dimensional sheath flow can be created by bringing a sample stream into contact with two symmetric sheath streams and manipulating the flow rates of the sheaths relative to the sample stream. The resulting sample stream in the flow channel extends from the floor to ceiling of the flow channel but is confined in the lateral direction by the flow ratio. For example, if the total flow rate of sheath fluid is $Q_{sheath}$ evenly between the two sheaths) and the sample flow is $Q_{sample}$, the lateral size of the sheathed sample flow is $$w_C = \left(\frac{Q_{sample}}{Q_{sheath}}\right) \times w$$

where w is the channel width. The use of a 250 um wide flow channel can yield a 25 um wide 1-dimensional sheath.

Figure 10:
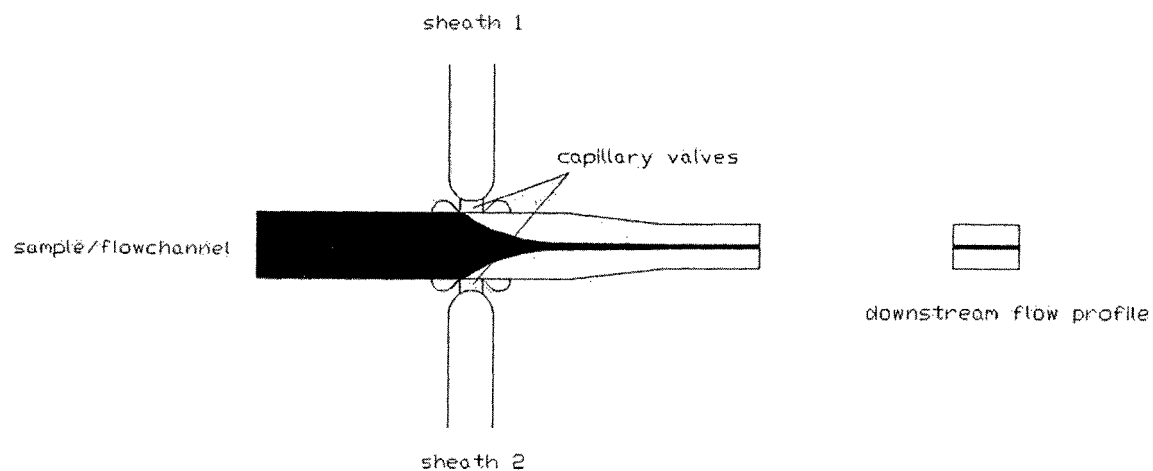
FIG. 10 illustrates a channel configuration suitable for an alternative one-dimensional sheath flow.

Implementation in a centrifugal format is straightforward as shown in FIG. 10. Sheaths 1 and 2 may be fed from a single sheath fluid reservoir, stopping at the two capillary valves connecting the sheath channels to the flow channel. Sample is then driven down the flow channel from an upstream position, and when the meniscus passes the exposed menisci of the sheaths, all three fluids flow. The relative impedances may be easily manipulated. For example, the upstream portion of the sample channel may be much smaller in dimensions than in the vicinity of the junction, creating a higher impedance than the sheath channels; or may be serpentine, having a much greater impedance by virtue of its greater length.

Liquid Rotation Due to Features in Channel Walls (Stripes)

In this method, sample and sheath streams are joined at a standard "T" junction, with the flow rate of the sample stream significantly lower than that of the sheath. In such a case, the sample initially clings preferentially to one wall in a thin ribbon. The placement of "stripes" angled at 45-degrees with respect to the flow, placed in the floor and ceiling of the channel, acts to cause circulatory motion. This pulls the sample stream away from the wall and toward the center of the channel. A roughly elliptical core flow is formed whose position and area are a function of the relative flow rates and number of stripes. The width, depth, and spacing of the stripes are of the same order of magnitude as the depth of the channel. Typically the channel is also shallower than it is wide.

Figure 11:
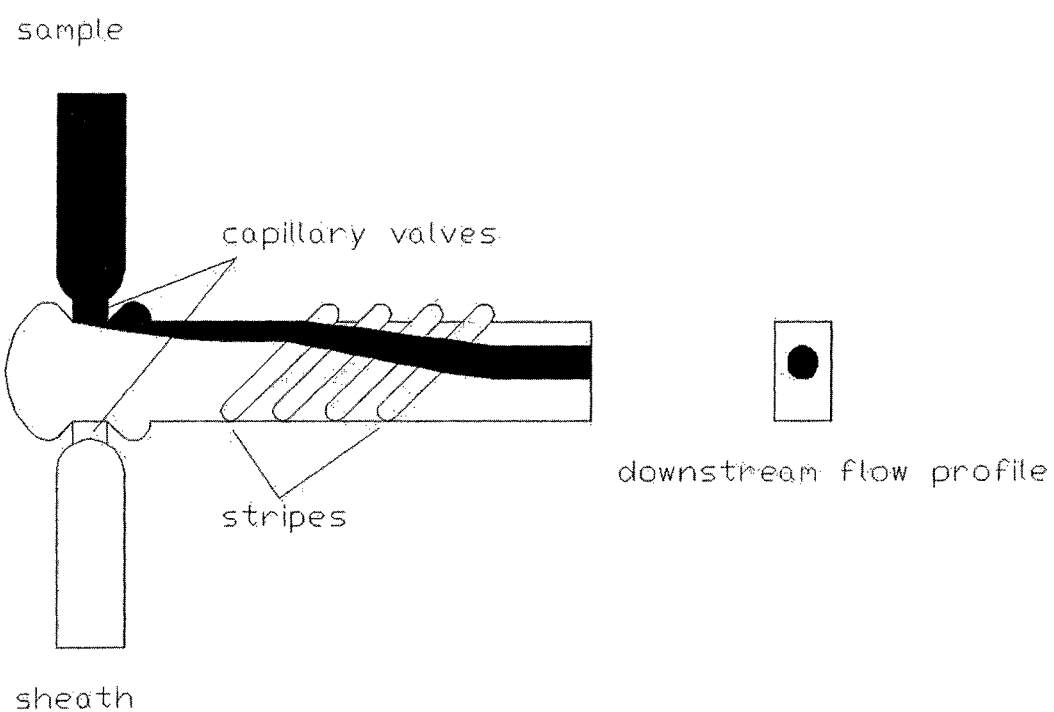
FIG. 11 illustrates a focusing method using liquid rotation.

Implementation in a centrifugal format is straightforward as shown in FIG. 11. The sheath and sample fluids are presented at capillary valves; upon acceleration to sufficient RPM, both valves fail and liquids are brought together. As in other cases combining sheath and sample flow, upstream impedances and pressures may be readily manipulated to create the desired flow ratio.

Full Two-Dimensional Sheath Flow.

It should be possible also to introduce full two-dimensional sheath flow. In this method, a 1-dimensional sheath flow is first generated. Introduction of sheath streams from below and above then act to compress the sample stream in the vertical direction, creating a true two-dimensional sheath.

Inertial Focusing

There are a large number of methods termed "inertial". These rely to varying degrees on the discreteness of the particles themselves to create focusing, not merely on the flow paths generated within the streamlines of the liquid as above. Some inertial methods also have a focusing component due to creation of focused streamlines as well. Nearly all of these methods operate at very low flow rates that cannot be obviously extended to the range required for quick analyses, e.g., the flow of several hundred uL of liquid in less than 1 minute. A secondary problem of most of these flow methods is that the fabrication demands are beyond what is reasonable to expect in high-volume manufacture in the near- to mid-term, since the sizes of structures are on the order of the sizes of the particles to be focused.

Figure 15:
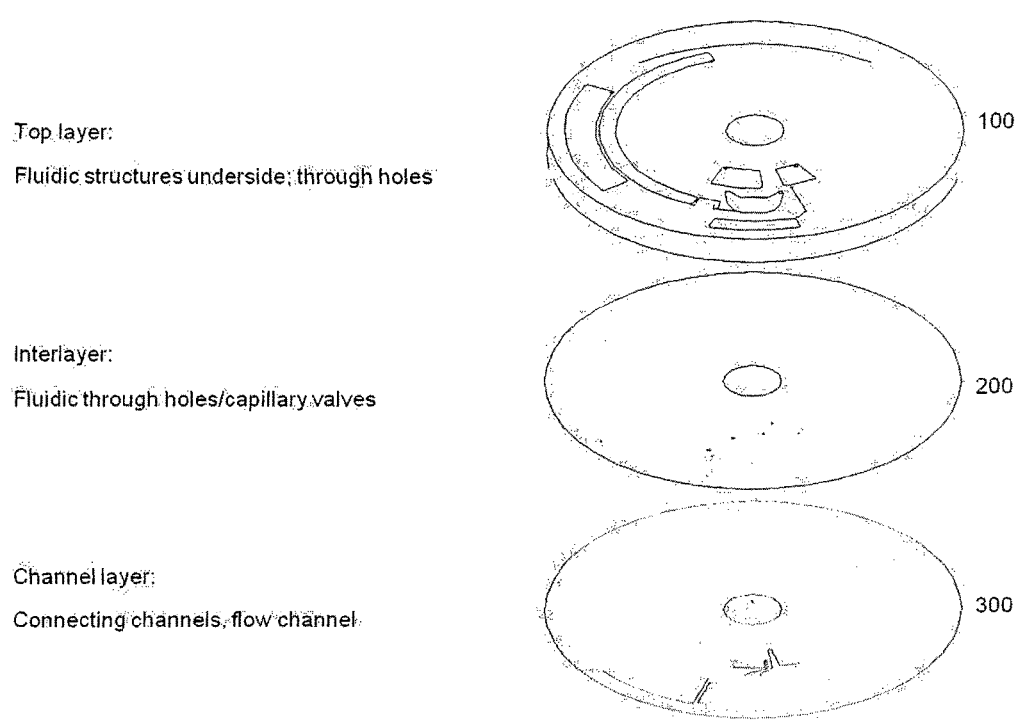
FIG. 15 illustrates a possible construction of microfluidic discs according to one embodiment.

An inertial focusing method that could be implemented in a microfluidic disc is illustrated in FIG. 15. This method uses expansions and contractions in the flow stream to induce vortices which have the effect of focusing the sample stream. For total flow rates <=5.5 mL/hour and sample: sheath ratios of 1:10, a structure with multiple contractions/expansions 350 um square and 53 um deep connected by channels 50 umW×53 umD and 300 um long has the effect of focusing the sample to a roughly cylindrical core (diameter ~18-20 um).

This is quite attractive from a fabrication and implementation point-of-view: All features are within one part that can be sealed with a lid. The sheath and sample fluids can be brought together in a typical "T" junction using capillary valves.

Detection Embodiments

In some applications, such as bead-based immunoassays, the detailed information for each particle afforded by flow cytometric detection is not necessary. For a single-plex immunoassay, only a single parameter is important: The fluorescence intensity, which is directly dependent on the binding of fluorescent labels to the bead surface and quantitatively reflects the analyte concentration. In these cases all beads are in principle identical—though there of course statistical fluctuations among them—and do not need to be measured individually. If beads can be measured in aggregate, a number of parameters are relaxed in overall system design: The device no longer must rotate during detection; the concentrations and beads/detection volume sizes do not need to be tailored to minimize multiple counting; the sampling rate of the detector no longer needs to be high. In addition to removing these constraints, bulk detection allows for an increase in signal-to-noise: By detecting many beads simultaneously within a small area of the disc, the overall fluorescent signal is increased and the ratio of fluorescent signal to background is much greater than with single-particle detection in flow.

Figure 13A:
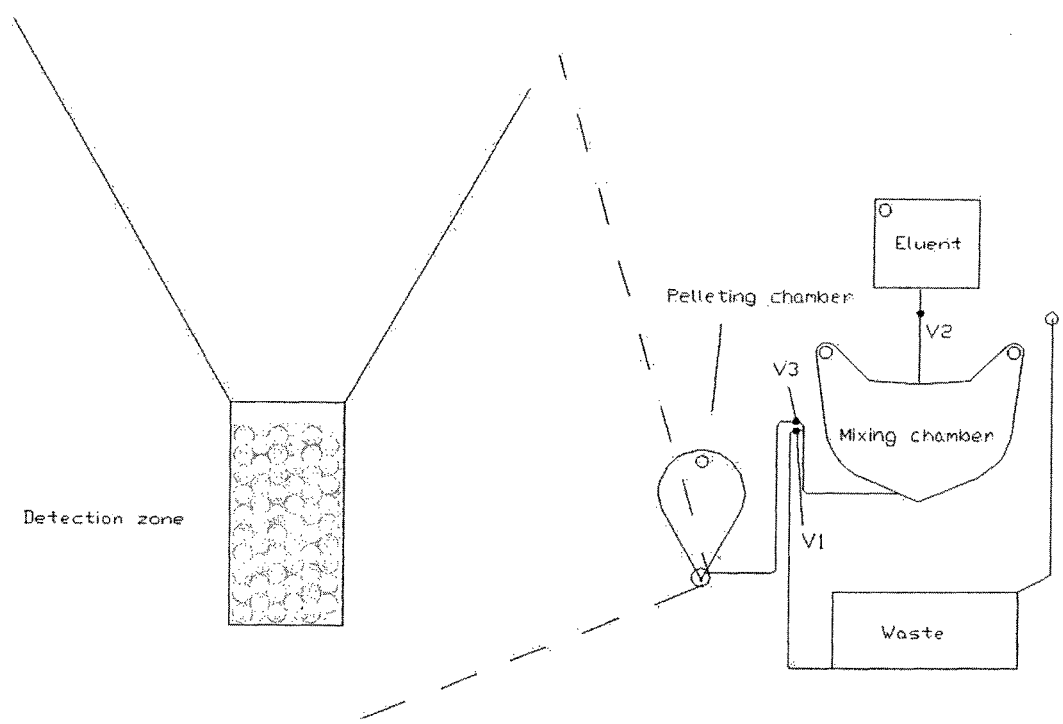
FIGS. 13*a*, 13*b* & 13*c* illustrate an alternative detection scheme in which beads are sedimented into a volume and then detected according to a preferred embodiment of the invention.

In measuring beads in bulk, beads may be immobilized against an internal surface of the disc. This can be done in several ways:

1. pelleting through centrifugation
2. trapping at constrictions of channels
3. trapping on a filter
4. magnetism FIG. 13a shows an implementation of pelleting through a centrifugation prior to detection of the beads in bulk.

Using the parameters of the immunoassay protocol above, the assay may provide 1000 beads of size 7.5 um. The minimum volume occupied by a packed bed of spherical particles is:

$$V \approx N_P \left(\frac{\sqrt{18}}{\pi}\right)\left(\frac{4}{3}\right)\pi\left(\frac{d}{2}\right)^3 = \frac{\sqrt{18}\, d^3}{6} N_P$$

For $N_P$=1000 particles of size d=7.5 um, this volume is ~3E5 um$^3$. If these particles are pelleted into a small volume 60 um deep, the area occupied by the beads (approximately 7-8 beads deep) is ~5e3 um$^2$ or ~71 um on side. This can be readily interrogated using low-cost optics.

In FIG. 13a, the assay is performed using the wash system of FIG. 5. Rather than injecting the washed beads into a flow channel, the beads are transported to a second pelleting chamber or particle receiving structure. The pelleting chamber is shaped such that there is a small, shallow detection zone at its outermost point. In this way fluorescent beads are compacted into a small area upon pelleting by centrifugation that may be interrogated in its entirety by the optical system, with a resultant amplification of fluorescent signal by a factor of 1000 relative to that of a single bead. It is envisaged that the invention can be used in applications with beads of much larger size. An amplification of even 10 (10 beads) would be significant such that signal/noise improvements with larger beads/more beads.

Control against loss of beads may be performed by interrogating a fraction of the volume, such as its outermost 50%.

Multiplexed assays may be accommodated through differential staining with well-separated emission peaks. For example, phycoerythrin (PE) and FITC can both be stimulated by absorption at 488 nm. The PE emission peak is at 575 nm and the FITC emission peak is at 520 nm. These can be spectrally-resolved using optical filtering methods known to those skilled in the art.

The use of a filter is a straightforward analogy to the above, wherein the beads are concentrated on a filter and then interrogated in bulk using the optical system. It will be appreciated that magnets may also be used to drag beads to a single detection point.

Figures 13B, 13C:
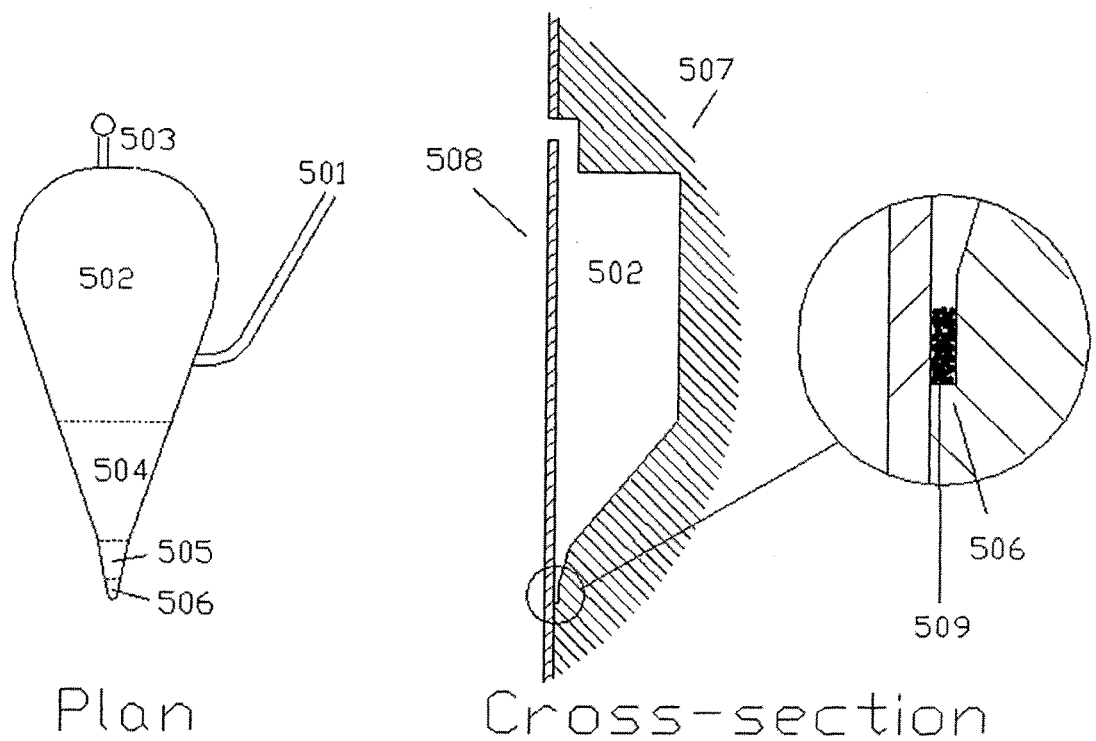

FIGS. 13b and 13c shows a plan view and cross sectional view of the bulk pelleting and detection chamber of FIG. 13 in greater detail. The structure is filled via a channel 501 entering the main body of the reservoir, 502; displaced air is vented through channel and vent 503. Below (radially outward) from the main body of the reservoir is a conical structure designed to funnel beads which are sedimented to outward on the disc at high rotation velocities. This may be composed of several 'cones" of varying dimensions. For example, a "steep" cone may tape the volume from the bulk thickness to a thickness of a few hundred microns 504, followed by a much more gradual slope 505. This combination of steep and shallow ensures that varying bead numbers occupy roughly the same area as viewed from above the disc ('plan' view). The fluorescent signal is proportional to the viewed area of beads; the bulk of the bead bed, below the surface, does not provide measurable fluorescence signal, as the incident radiation is strongly scattered by the beads as it penetrates below the first few layers of beads.

Because of this feature—strong light scattering due to the packed beads—the detection structure shown also has a further, very thin final sedimentation "finger" 506. This is typically 50 not-60 um deep and ~100 um wide×~300 um long. The precise dimensions are that important, but smooth edges are useful in preventing air—initially present in the chamber—from being trapped as a bubble in region 506.

Clinical Chemistry Applications

Standard clinical chemistry assays may be performed on either whole blood as applied to the device or on plasma separated from the whole blood sample.

A variety of assay chemistries may be employed, including chromogenic or fluorogenic chemistries utilizing enzyme systems to generate coloured or fluorescent products from substrates either in the presence or absence of an analyte of interest. These assay systems may be used in a variety of ways, including bulk fluorescent measurement; optical density or absorbance measurements in transmission through an optical cuvette on the microfluidic disc or in the presence of reflective media; or through reflectance measurements from matrices which are impregnated with reagents and evolve the products appropriate for detection.

In preparing matrices according to the invention, reagents advantageously used to detect and more preferably quantitate an amount of a component of a biological fluid sample are impregnated into the matrix. As a non-limiting example, creatinine is detected according to the invention using a series of coupled reactions, in which creatinine is first converted to N-methylhydantoin and ammonia by creatinine iminohydrolyse; the final step of the cascade is the conversion of generated hydrogen peroxide to detectable product using hydrogen peroxidase and for example tetramethyl blue as a substrate. Fabrication of the reflectance matrix involves multiple soaking and drying steps prior to insertion into the microfluidic disc.

Materials used to prepare said matrices include but are not limited to derivatized nylons, nitrocellulose, fiberglass and polyesters, most preferably having a pore size of 0.2-2.0 um, typically comprising a positively-charged nylon matrix having a pore size of about 0.8 um. The upper limit on pore size of matrix is chosen to inhibit or prevent blood cell entry into the matrix. The matrix is positioned in assay chamber to be in fluidic contact with a channel leading from the sample metering chamber. The matrix is further impregnated with immobilized reagents which produce a detectable product proportional to the amount of analyte in a blood sample. Most preferably, the detectable product is a coloured product, i.e., a product absorbing light at a detectable, most preferably a visible, wavelength.

Figure 14:
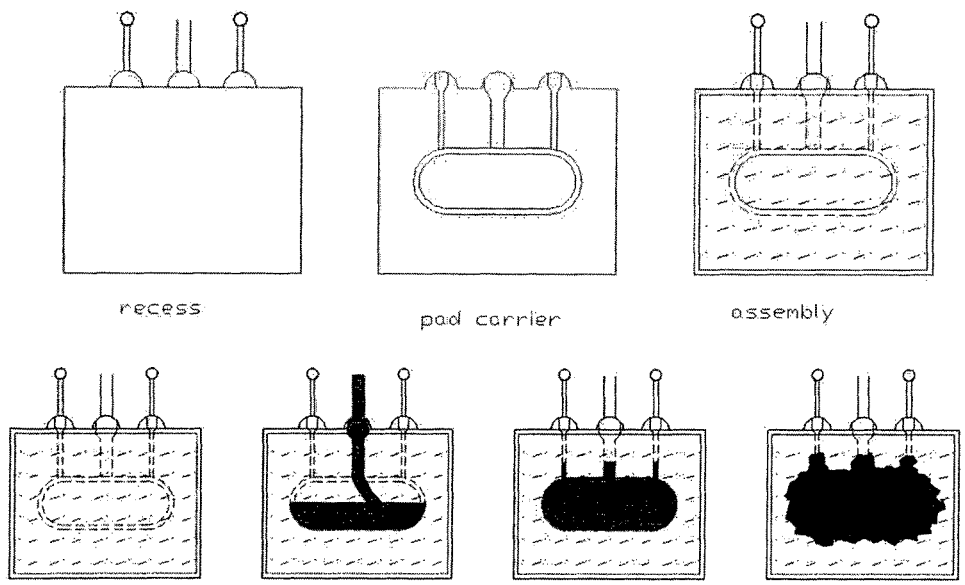
FIG. 14 illustrates the construction and use of a dried chemistry, porous pad for colorimetric ("clinical") chemistry assays.

The reagent pad may be installed as in FIG. 14. A recess formed in the fluidic surface of the disc is formed with a channel to carry sample as well as one more air-displacement channels for removal of air displaced by sample. A pad carrier is formed that has substantially the same lateral dimensions as this recess such that when pressed into the recess a liquid-tight press-fit is obtained. The channels and air displacement channels of the disc seal with a corresponding channel and air-displacement channel on the under surface of the pad carrier. The pad carrier's lower surface also contains a "bowl" for sample with a large through-hole communicating to its upper surface. To this upper surface is adhered the reagent-impregnated reflectance pad.

EXAMPLES

A possible construction of microfluidic discs according to the invention is shown in FIG. 15. This microfluidic disc consists of three main components: A fluidic layer 100 which contains the majority of fluidic structures such as reservoirs, channels, passive valves, and reagents in the form of liquid reagents or dried reagents; a thin interlayer 200 containing primarily through holes; and a lower or channel layer 300. Communication between 100 and 300 is via the through holes in 200. Such a construction is useful when making three-dimensional architectures requiring liquid 'crossovers', in which channels must pass over one another.

It is recognized that this construction is in no way limiting. Microfluidic discs may be formed by sealing a fluidic layer with an essentially featureless layer or thin film, without additional channels or through holes. In one construction there is provided a featureless sealing film and a disc.

Immunoassay and Clinical Chemistry Device

Figure 16:
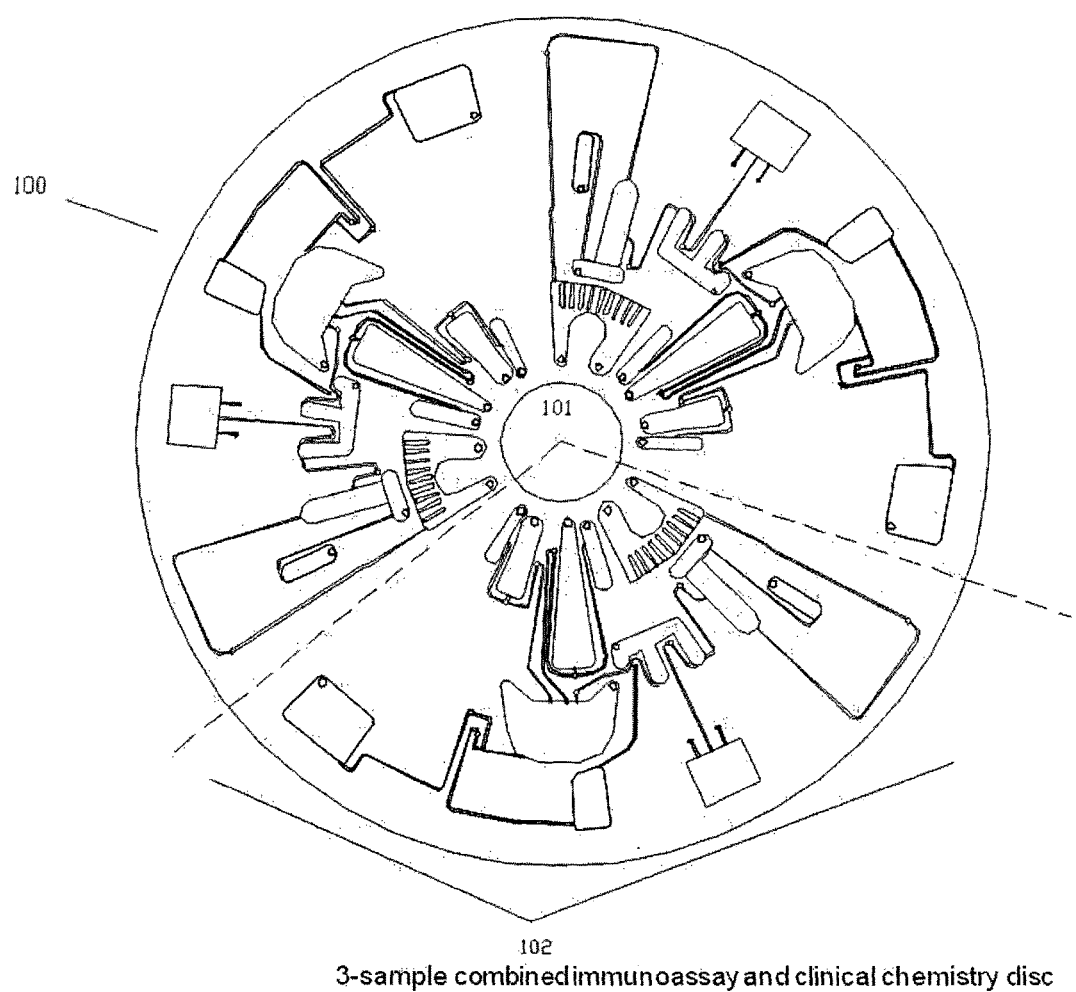
FIG. 16 illustrates a disc of the invention, according to one embodiment.

A disc of the invention is shown in FIG. 16, where only the fluidic layer 100 is illustrated. This disc construction is comprised of a structured substrate and featureless sealing film. This disc is designed to perform two types of assay: One immunoassay, which may be multiplexed through the use of multi-coloured beads or multi-coloured labels; and a clinical chemistry assay developed for reflectance detection. The disc has a central mounting feature 101 which may be a hole or other feature designed to positively lock the disc to the hub of a rotary motor. This disc is designed to perform assays on three independent samples; one sample is measured in the set of assay structures 102.

It should be noted that central feature 101 is only one way in which the disc may be attached to the rotary motor; attachment features at other radii may be used, for example, symmetrically-placed pins on a rotor may mate with holes on the microfluidic disc.

While this disc is designed for use with manually pipetted buffers and liquid reagents as well as whole blood sample, it is recognized that the use of blister pouches or bags or other liquid reagent means may be employed, and application of whole blood may be done using blood-draw and application devices or by lancing a finger and applying the resultant blood droplet to a port of the disc.

Figure 17:
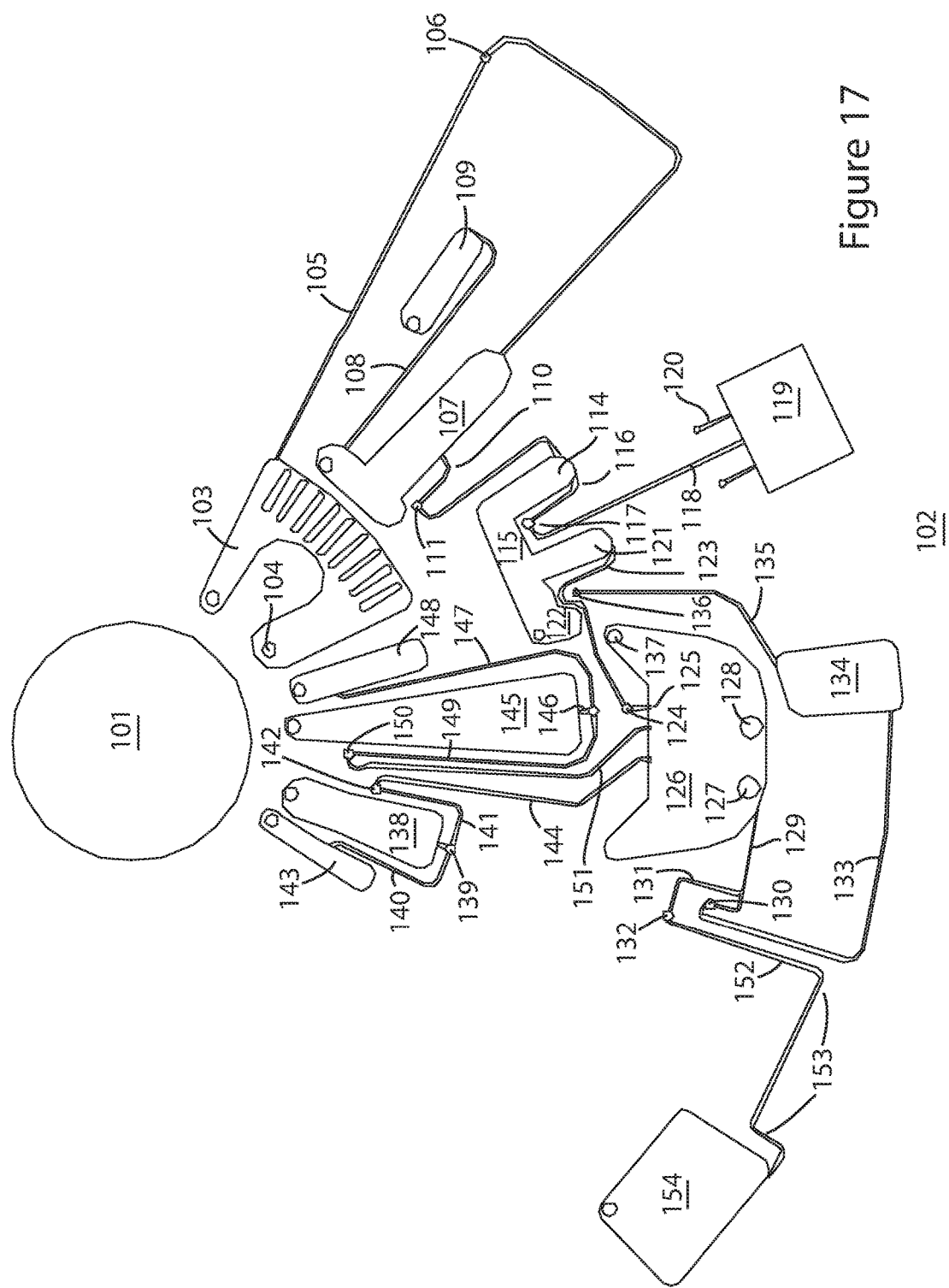
FIG. 17 illustrates the detailed construction of one sample-processing assay structure, according to one embodiment.
Figure 18A:
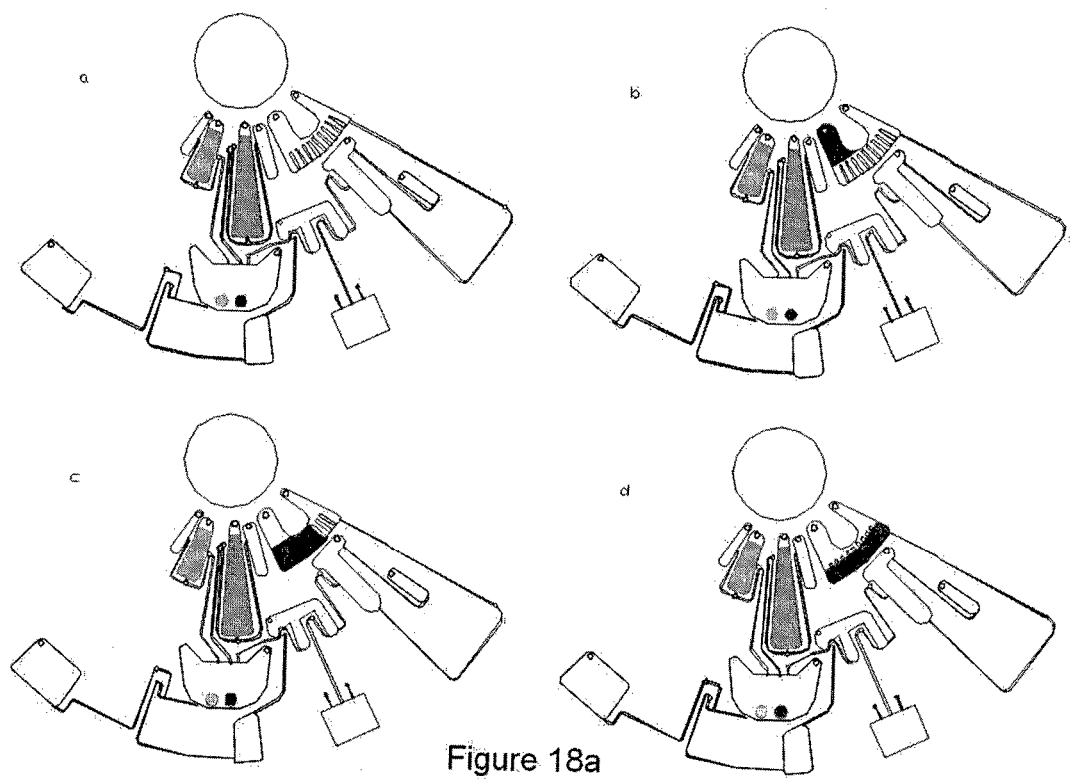
FIG. 18 illustrates the function of the microfluidic assay structure.
Figure 18B:
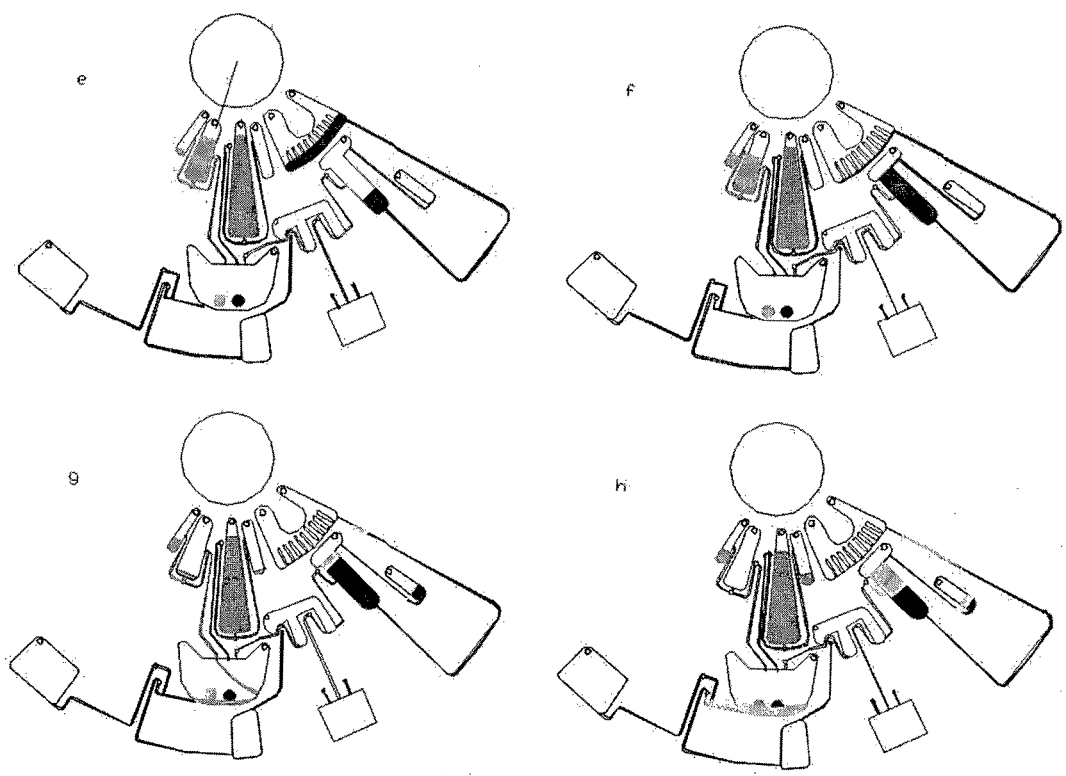
Figure 18C:
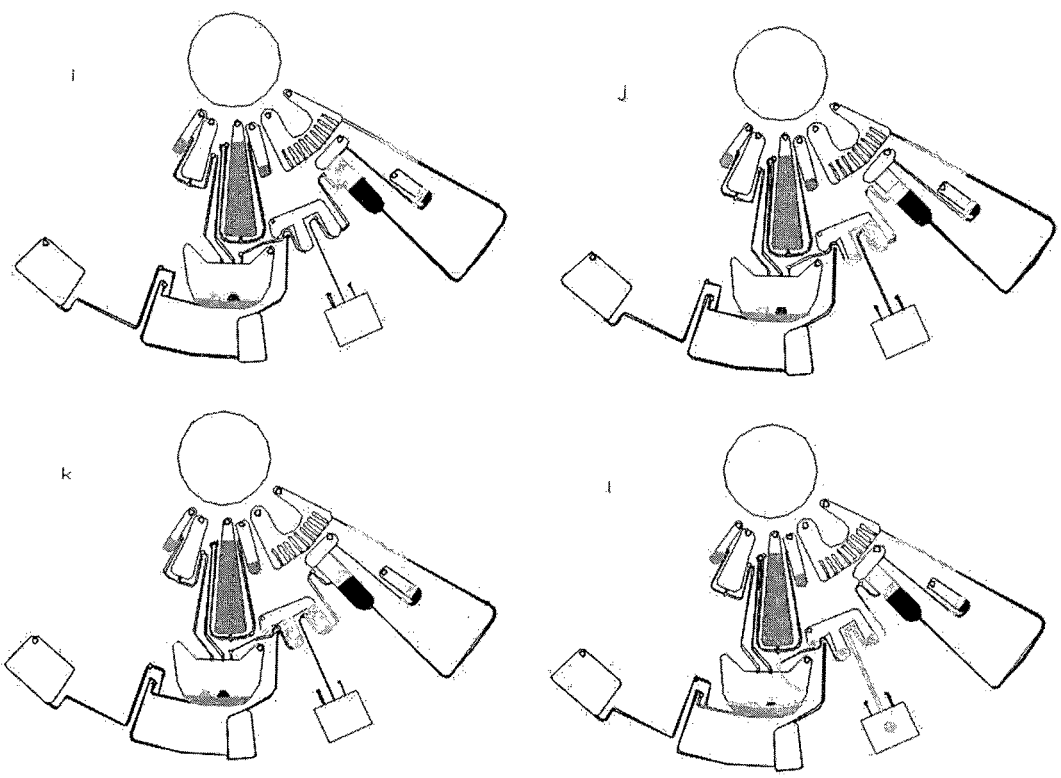
Figure 18D:
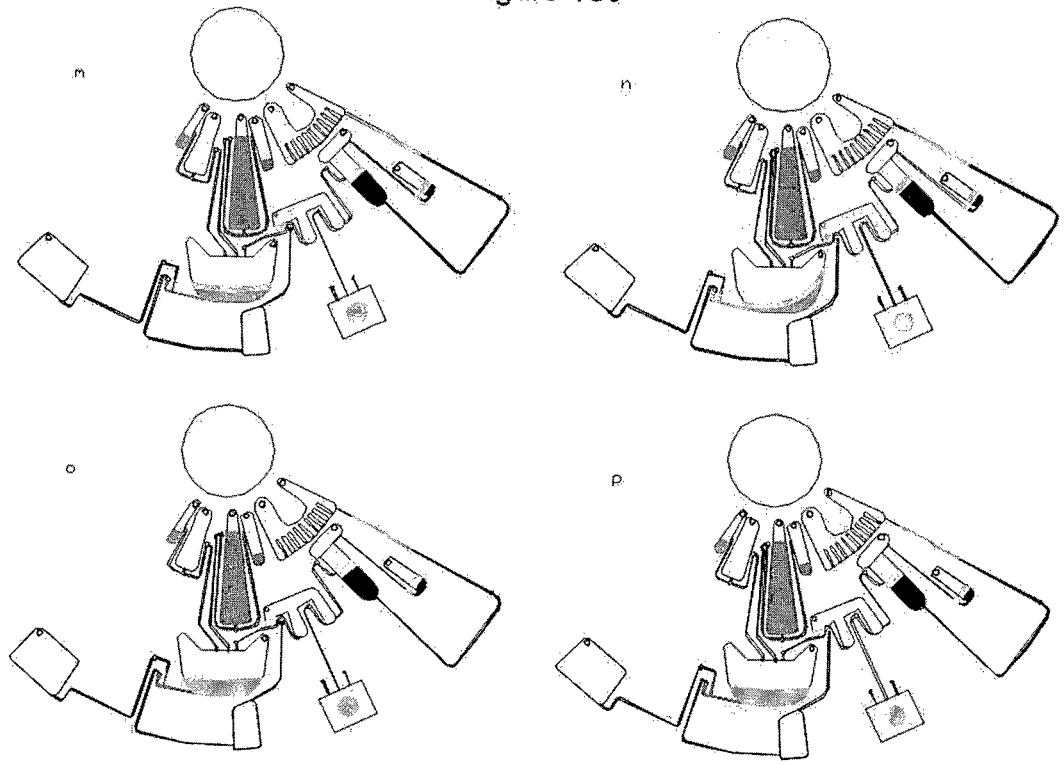
Figure 18E:
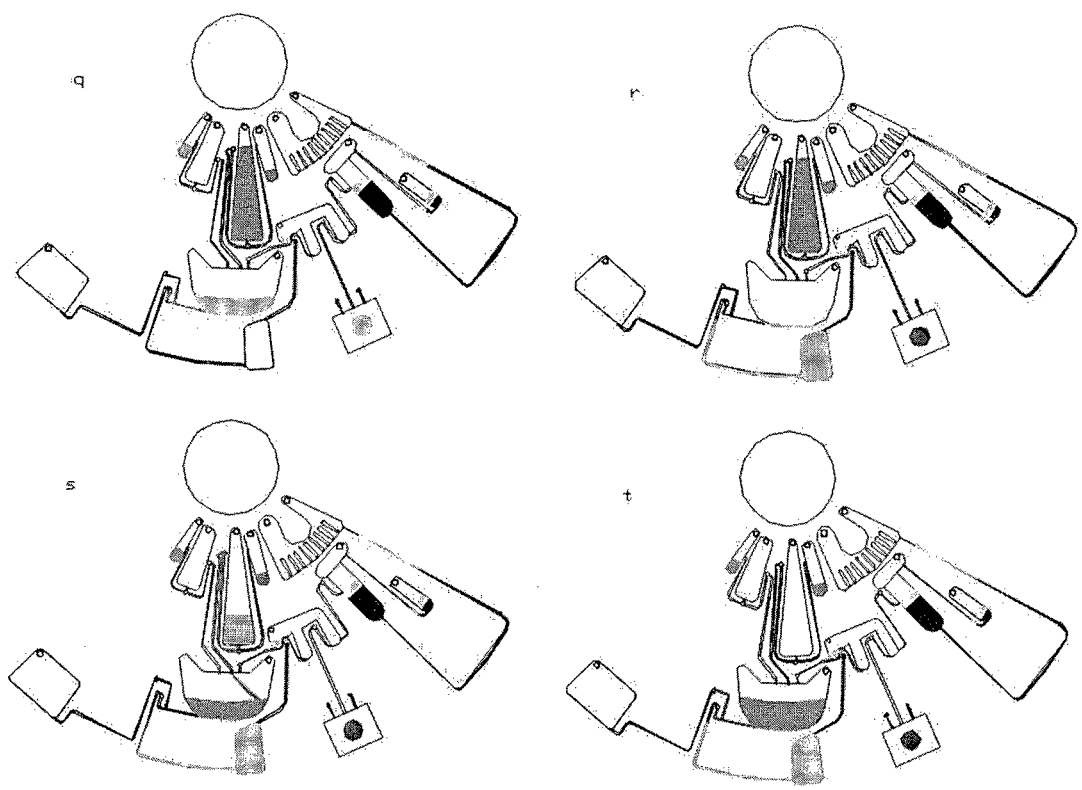
Figure 18F:
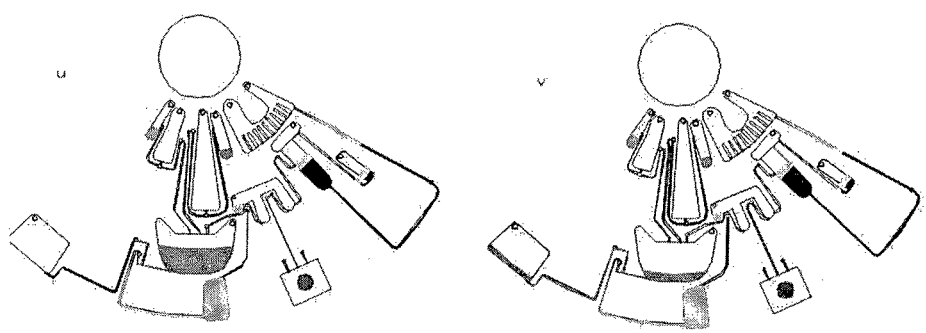

FIG. 17 illustrates the detailed construction of one sample-processing assay structure. The designated features will be described in relation to their function.

FIG. 18 illustrates the function of the microfluidic assay structure.

The disc contains resuspension buffer present in reservoir 138 and elution buffer in reservoir 145. In prototypes, these buffers may be pipetted onto the disc. In production, these buffers may be present in blister pouches. Blister pouches may be opened in a variety of ways:
  Frangible seals opened by rotation. Pressure generated within the reagent containers act to open weak seals in the pouches
  Rupture by instrument. The disc may be designed with a mechanism that allows structures on the rotary hub of the instrument to puncture the blisters
  Rupture by embedded pins/sharp surfaces. Embedded pins, either added in manufacture or directly moulded into the plastic, may be present in the outer edge of the reservoirs; upon spinning at sufficient rate, the force of the pouches against these pins ruptures the pouches Blood is applied by the user to port 104 of the blood entry structure 103, which may have a textured surface designed to prevent the blood from inadvertently flowing into further channels and structures prior to rotation. These structures may include narrow "trenches" perpendicular to the desired flow path, which act to prevent inadvertent wetting of the surface prior to rotation. An air exhaust port may exit in the entry structure, or alternatively, displaced air is vented through further fluid channels.

The disc is installed on the rotary motor and a spin profile is initiated.

At the initial rotation rate W1 (typically 200-400 RPM), the blood is driven by centrifugal force to fill the entry structure and then (panel d) to enter channel 105. Optionally, channel 105 may have a capillary valve 106 disposed within, in order to halt further flow of blood until the inner meniscus remaining within 103 has stabilized into a shape perpendicular to the radius. Increase of rotation rate to W2>W1 defeats valve 106; the rotation rate may be lowered again.

The blood is now pumped centrifugally into the separation column 107, which is connected via channel 108 to an overflow chamber 109. Chamber 109 has a means for venting displaced air, the regions of the separation structure 107 proximal to the disc's centre may also have a venting means. (Panels e-f). At the same time, resuspension buffer present in 138 is released through a capillary vale 139 into channels 140 and 141. Capillary valve 142 in channel 141 impedes further flow through that channel; flow through 140 continues into an overflow reservoir 143, useful for precisely determining the remaining volume of buffer within reservoir 138. This is illustrated in panels e-f.

The rotation rate is increased to W3>(W1,W2), typically in the range of 1000-3000 RPM, in order to perform separation of the blood into plasma and packed cell fraction. Any excess blood in the separation structure is driven completely into the overflow volume 109. Panel g illustrates the onset of the separation process, with blood cells packing toward the outer surface of 107

During the plasma separation process, capillary valve 142 releases the resuspension buffer, which is delivered through channel 144 to the mixing chamber 126. Present in mixing chamber may be dried reagents, for example, dried immunomodified beads 127 and dried fluorescent dye 128.

Plasma separation continues. During this separation, blood and plasma are present in side-arm channel 110 connected to the separation volume 107, but retained by capillary valve 111.

Also during separation, the capillary valve 146 for the elution buffer is defeated by centrifugally-initiated pressure, leading to overflow of excess buffer into reservoir 148 through channel 147, in analogy with the resuspension buffer.

In panel j, the rotation rate has been increased momentarily to W4>W3, and typically slowed to more moderate level. This defeats capillary valve 111 and allows plasma to be decanted from the inner portion of 107, to the level where the channel 110 joins the chamber (at which point air is drawn into 110, separating the plasma aliquot from the retained packed blood cells). The plasma first flows into metering reservoir 114 and overflows through passageway 115 into $2^{nd}$ metering reservoir 121 and overflow volume 122. Reservoir 114 meters plasma adequate for performance of the reflectance-based assay, while reservoir 121 meters a volume appropriate for immunoassay. Each metered volume is retained by a capillary valve (117 and 124, respectively).

In panel I, the rotation rate is spiked to W5 and then slowed, defeating capillary valves 117 and 124.

The plasma passing through valve 117 moves via channel 118 to the reflectance structure 119, which is embedded with reagents appropriate for creating a fluorescent or coloured product based on analytes within the plasma. Displaced air is vented through vents 120.

The plasma passing through valve 124 enters the mixing chamber 126 via channel 125.

Rotation is slowed. A gentle agitation is performed as shown in panel n, by slowing and accelerating the disc, typically with accelerations of 1000-10,000 RPM/sec but at an overall slow velocity of a 100-500 RPM. This agitation may be "unidirectional", i.e., the disc may be rapidly decelerated from its 500 RPM to rest and then slowly accelerated back to 500 RPM; and then stopped again, and cycled thusly. Or the agitation may be bi-directional, with the disc changing rotation direct every half-cycle. Unidirectional agitation is particularly useful to minimize pressure transients on the capillary valves attached by channels 129 and 131 to the exit (bottom) of the mixing chamber, by applying the high accelerations or decelerations in a tangential direction opposite to that which the channels 129 and 131 exit from the chamber.

In panel o, the reagents have been completely resolubilized and mixed with sample and resuspension buffer and the beads are now dispersed homogeneously in solution. In the reflectance structure, the chemical reaction leading to detectable product continues. The disc may be continually agitated as the immunoassay is incubated in the mixing chamber Rotation rate is increased to W5, typically 500-2500 RPM, in order to pellet the beads in the mixing chamber, as shown in panel p.

In panel q, the chemical reaction that produces detectable reaction products in the reflectance pad has gone to completion. Detection may occur by measurement of reflection at 1-several wavelengths while the disc is rotating at a low rate.

A spike in rotational velocity to W6, with subsequent reduction in rotation rate, defeats capillary valve 130 and allows supernatant of the sedimented beads in the mixing chamber to travel through channel 133 to waste reservoir 134, which is vented by a narrow channel 135 and port 136. As shown in panel r, the reservoir 134 may be sized such that a small volume of supernatant is retained within the mixing chamber: As 134 fills, eventually liquid rises within channel 135, and when the meniscus of this liquid is at the same radial position as the meniscus of retained fluid in 126, fluid motion ceases.

In panel r, rotation rate is spiked to velocity W7 and elution buffer is released through capillary valve 150 into channel 151 and thence into the mixing chamber. Because the waste chamber is full and the air exhaust channel 135 is of narrow diameter and extends radially inward of the mixing chamber, fluid does not travel through channel 133 to waste, and an elution volume greater than that of the initial sample+resuspension volume may be accommodated. This is shown in panel t.

Gentle agitation re-suspends the beads, leading to a final state with beads homogeneously distributed in the elution buffer within the mixing chamber in panel u.

Finally, rotation rate is spiked to velocity W7 and then reduced, defeating capillary valve 132 and allowing the bead-carrying fluid into channel 152. A section of 152 is the flow channel region 153, arranged tangentially at a fixed radius for inspection by the detection system. This fluid is further driven into waste reservoir 154 with venting port. Detection occurs as fluid flows through 153. As necessary, further agitation steps may be used to prevent undue settling of the beads in the remaining solution within the mixing chamber. It is also recognized that the rotation rate may vary during this step, starting at a low rate and increasing in order to maintain a substantially constant flow rate.

It will be appreciated that replacement of the flow channel with its waste chamber with the unified bulk pelleting chamber—which acts as its own waste chamber—is straightforward, where the detection step involves a high-speed centrifugation (e.g., 7200 RPM for 30 sec) followed by detection.

Sheath Flow

Figure 19:
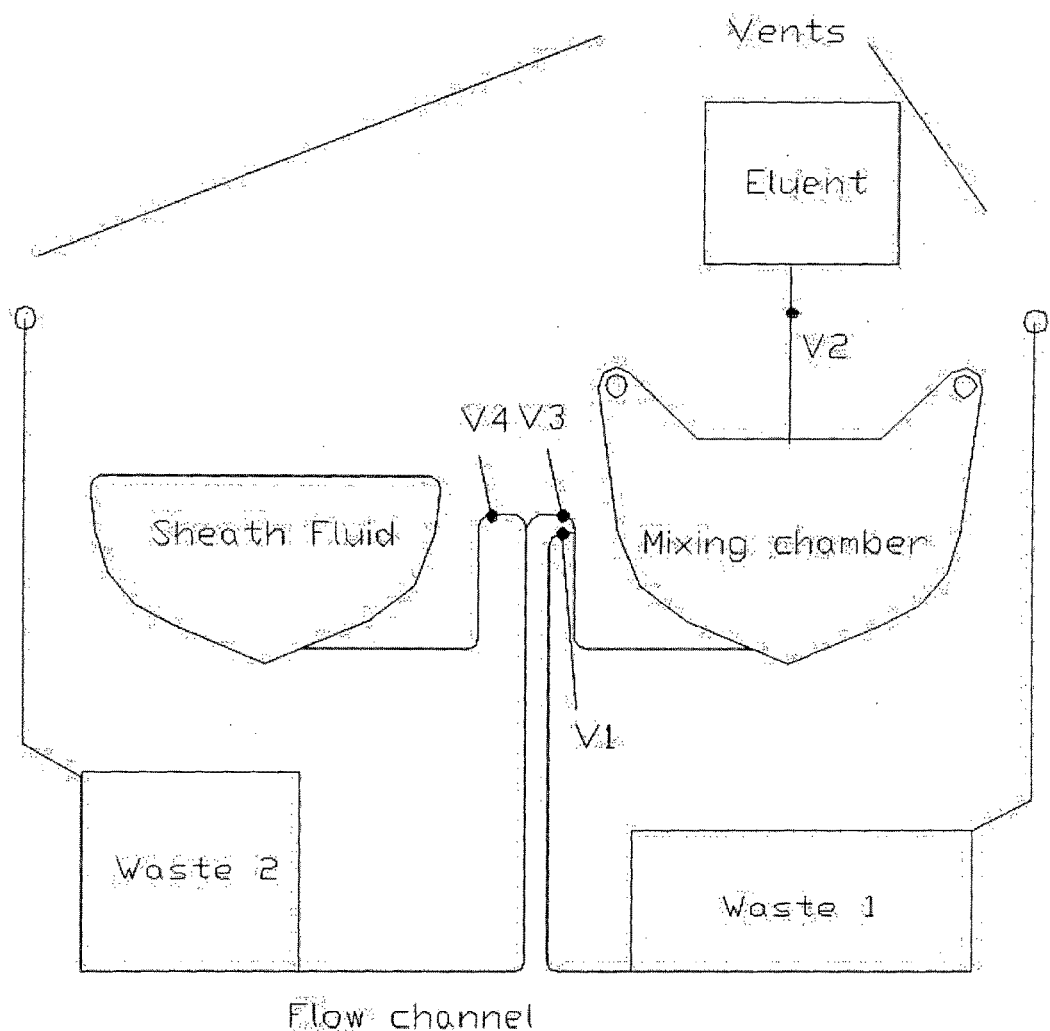
FIG. 19 illustrates a microfluidic disc appropriate for the creation of sheath flow in conjunction with FIG. 5.

FIG. 19 illustrates a microfluidic disc appropriate for the creation of sheath flow. Here it is illustrated in conjunction with the wash method of FIG. 5. In addition to the mixing chamber, eluent chamber, waste chambers, and capillary valves and channels already discussed, a reservoir containing sheath fluid is present, separated from the flow channel and mixing chamber by capillary valve V4. It is understood that the sheath fluid may be present in a large reagent pouch or blister prior to being driven to this sheath fluid reservoir at an earlier stage in the integrated disc's operation.

Figure 20:
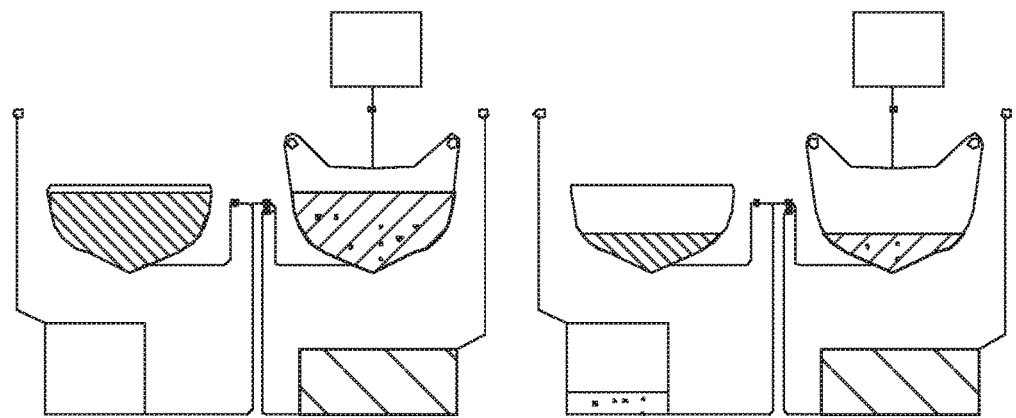
FIG. 20 illustrates flow of sample and sheath fluid into a flow channel and then to a waste reservoir.

Wash steps proceed as in the previous example. Rotational rate is spiked to release the bead-containing solution from the mixing chamber into the flow channel through valve V3; simultaneously, sheath fluid is driven past valve V4, joining the sample solution in the flow channel. This is illustrated in FIG. 20. Details on the construction of the fluid junctions for sheath flow are given below.

As discussed above, the desired flow ratio for sheath flow is determined by $$\frac{Q_{sheath}}{Q_{sample}} = \frac{A_{sheath}(r)}{A_{sample}(r)}$$

FIG. 20 shows a disc laid out to provide such a 10:1 sheath flow. The sheath reservoir is twice the depth of the mixing chamber. It is shaped such that it narrows—and the cross-sectional area decreases—with increasing radial position, in the same way that the mixing chamber grows narrower, thus maintaining the flow ratio.

Figure 21:
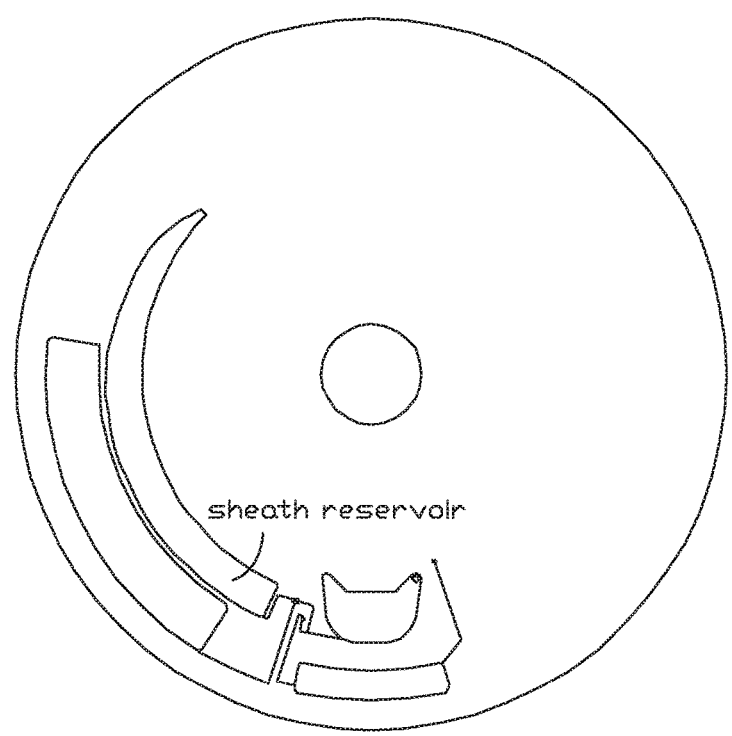
FIG. 21 shows a disc laid out to provide such a 10:1 sheath flow.
Figure 22:
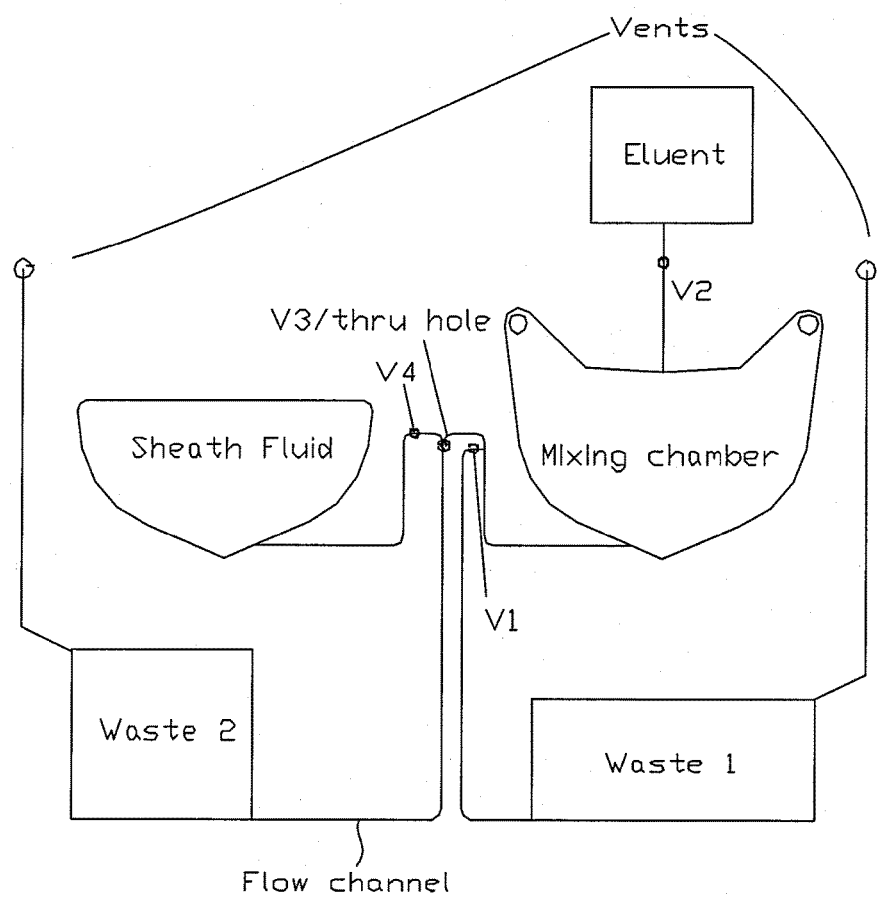
FIG. 22 illustrates a specific embodiment of the invention in which fluid enters from a $2^{nd}$ layer into the first layer through the "floor" of the channel also illustrated in FIG. 9.

Implementation of sheath flow on the microfluidic disc can use the methods provided above, where the details of the junction between sheath and sample solutions determines the type of sheathing. For example, combination of the overall structure shown in FIG. 2, with the non-coaxial sheath of FIG. 12, can be done by creating a three-part disc as in FIG. 15. This is shown in FIG. 21. The solution to be analyzed travels in the lower channel layer from the mixing channel to a point where it joins the main flow channel through a through-hole in the interlayer. This through-hole can act as valve V3 in FIG. 22. The velocity spike which releases the sheath fluid through valve V4 is used to trigger the flow of the sample, and focused sheath flow takes place.

It is recognized that there are many variations on these basic ideas. For example, the use of siphons may supplement that of capillary valves. Siphons may also be used in conjunction with capillary valves: Capillary valves can prevent the "priming" of siphons at undesired, low rotational velocities; bursting a valve may be a part of another step on the disc; subsequent slowing of the disc leads to priming of the siphon, followed by flow.

The embodiments in the invention described with reference to the drawings comprise a computer apparatus and/or processes performed in a computer apparatus. However, the invention also extends to computer programs, particularly computer programs stored on or in a carrier adapted to bring the invention into practice. The program may be in the form of source code, object code, or a code intermediate source and object code, such as in partially compiled form or in any other form suitable for use in the implementation of the method according to the invention. The carrier may comprise a storage medium such as ROM, e.g. CD ROM, or magnetic recording medium, e.g. a floppy disk or hard disk. The carrier may be an electrical or optical signal which may be transmitted via an electrical or an optical cable or by radio or other means.

In the specification the terms "comprise, comprises, comprised and comprising" or any variation thereof and the terms include, includes, included and including" or any variation thereof are considered to be totally interchangeable and they should all be afforded the widest possible interpretation and vice versa.

The invention is not limited to the embodiments hereinbefore described but may be varied in both construction and detail.

The invention claimed is:

1. A microfluidic system for processing biological samples comprising:
    a rotary motor;
    a means for controlling said motor;
    a platform coupled to the rotary motor and adapted to provide at least one particle-washing structure and particle receiving structure adapted for receiving sedimented particles washed in the particle washing structure; and a detection zone for detection of washed particles in the particle receiving structure while the platform rotates, wherein the particle receiving structure comprises a pelleting chamber which is tapered to a point at one end such that the detection zone is defined at its outermost point, and wherein the particle washing structure comprises a bifurcated outlet channel which leads both to a waste reservoir and the particle receiving structure, in which the outlet channel emerges from the particle washing structure at a radius that is less than the maximum radial position of the radially distal wall from the centre of rotation of the particle washing structure.

2. The microfluidic system as claimed in claim 1 wherein the particles are selected from the group consisting of immuno-modified beads, fluorescently labelled immuno-modified beads representative of characteristics of said biological sample, and combinations thereof.

3. The microfluidic system as claimed in claim 1 wherein the detection zone is adapted to cooperate with an optical system while the platform rotates.

4. The microfluidic system as claimed in claim 1 wherein the tapered end of the pelleting chamber further comprises an elongated thin channel portion closed at one end to allow particles to sediment in the channel under centrifugal force.

5. The microfluidic system as claimed in claim 1 wherein the detection zone is shaped such that the particles are compacted into a small area upon pelleting by centrifugation.

6. The microfluidic system as claimed in claim 1 wherein the particles are washed in a particle washing structure that is adapted for the sedimentation of particles under the influence of centrifugal force.

7. The microfluidic system as claimed in claim 1 in which a port or channel is adapted to evacuate air displaced from the waste reservoir by fluid flowing through the particle receiving structure.

8. The microfluidic system as claimed in claim 1 in which the geometric constrictions of capillary dimensions and expansions within the bifurcations of the outlet channel act to resist flow at a first rotational velocity of the platform when the particle washing structure contains fluid but configured to allow fluid to flow at a second higher rotational velocity.

9. The microfluidic system as claimed in claim 1 wherein a defined volume will be retained within the particle washing structure when emptying into the waste reservoir in response to centrifugal force.

10. The microfluidic system as claimed in claim 9 in which the retained fluid comprises particles.

11. The microfluidic system as claimed in claim 9 in which the waste reservoir comprises a defined waste volume approximately equal to the desired sample volume.

12. The microfluidic system as claimed in claim 9 in which the waste reservoir comprises a defined waste volume approximately equal to the desired sample volume and a channel is provided to carry air displaced from the waste reservoir.

13. The microfluidic system as claimed in claim 9 in which the waste reservoir comprises a defined waste volume approximately equal to the desired sample volume and a channel is provided to carry air displaced from the waste reservoir and the channel is directed radially inward from the waste reservoir, ending at a port or other channel radially inward of the liquid level to be achieved within the particle washing structure while the platform is under rotation and the washing chamber is filled with the maximum volume of operating fluid.

14. The microfluidic system as claimed in claim 9 in which the waste reservoir comprises a defined waste volume approximately equal to the desired sample volume and a channel is provided to carry air displaced from the waste reservoir and the interior volume of the particle washing structure is greater than that of the maximum designed volume of operating fluid, to enable the use of air within the particle washing structure in mixing the fluid while under rotational accelerations and decelerations.

15. A method for processing biological samples comprising:
coupling a platform to a rotary motor;
configuring the platform with at least one particle-washing structure and particle receiving structure;
receiving sedimented particles in the particle receiving structure washed in the particle washing structure; and
detecting washed particles in the particle receiving structure while the platform rotates,
wherein the particle receiving structure comprises a pelleting chamber which is tapered to a point at one end such that the washed particles are detected at its outermost point and wherein the particle washing structure comprises a bifurcated outlet channel which leads both to a waste reservoir and the particle receiving structure, in which the outlet channel emerges from the particle washing structure at a radius that is less than the maximum radial position of the radially distal wall from the centre of rotation of the particle washing structure.

* * * * *